(12) United States Patent
Oda

(10) Patent No.: US 9,335,422 B2
(45) Date of Patent: May 10, 2016

(54) RADIOGRAPHIC IMAGING DEVICE, RADIOGRAPHIC IMAGING SYSTEM, METHOD OF CONTROLLING RADIATION DETECTION SENSITIVITY AND PROGRAM STORAGE MEDIUM

(71) Applicant: FUJIFILM CORPORATION, Tokyo (JP)

(72) Inventor: Yasufumi Oda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 223 days.

(21) Appl. No.: 13/943,270

(22) Filed: Jul. 16, 2013

(65) Prior Publication Data

US 2014/0021365 A1    Jan. 23, 2014

(30) Foreign Application Priority Data

Jul. 17, 2012  (JP) .................................. 2012-158928

(51) Int. Cl.
| | |
|---|---|
| *F21V 9/16* | (2006.01) |
| *G01T 1/17* | (2006.01) |
| *G01T 1/20* | (2006.01) |
| *H04N 5/32* | (2006.01) |
| *A61B 6/00* | (2006.01) |
| *H04N 5/232* | (2006.01) |

(52) U.S. Cl.
CPC . *G01T 1/17* (2013.01); *A61B 6/548* (2013.01); *G01T 1/2018* (2013.01); *H04N 5/23241* (2013.01); *H04N 5/32* (2013.01)

(58) Field of Classification Search
CPC ............. H03G 2201/40; G02F 1/0123; H04B 10/6911
See application file for complete search history.

(56) References Cited

U.S. PATENT DOCUMENTS

| | | | | |
|---|---|---|---|---|
| 5,920,070 | A | * | 7/1999 | Petrick et al. ............ 250/370.09 |
| 6,399,950 | B1 | * | 6/2002 | Kimura et al. ........... 250/370.09 |
| 6,404,854 | B1 | * | 6/2002 | Carroll et al. ................. 378/98.8 |
| 2001/0012330 | A1 | * | 8/2001 | Ogura et al. ..................... 378/95 |
| 2002/0050568 | A1 | * | 5/2002 | Nonaka ................... H01L 27/00 250/370.09 |
| 2003/0178552 | A1 | * | 9/2003 | Hofmeister et al. ...... 250/214 R |
| 2009/0224235 | A1 | | 9/2009 | Kitamura et al. |
| 2011/0240865 | A1 | * | 10/2011 | Frach et al. .................... 250/362 |

FOREIGN PATENT DOCUMENTS

| | | |
|---|---|---|
| JP | H11-155847 A | 6/1999 |
| JP | 2009-212389 A | 9/2009 |
| JP | 2011-185622 A | 9/2011 |

OTHER PUBLICATIONS

A Japanese Office Action issued in corresponding Japanese Patent Application No. 2012-158928 on Jun. 23, 2015, along with an English translation thereof.

* cited by examiner

*Primary Examiner* — David J Makiya
*Assistant Examiner* — Kenneth J Malkowski
(74) *Attorney, Agent, or Firm* — Birch, Stewart, Kolasch & Birch, LLP

(57) ABSTRACT

A radiographic imaging device including: a detector that detects an irradiation start of radiation irradiated in imaging of a radiographic image; a derivation unit that derives an irradiation amount of radiation that will be irradiated within a specific period of time based on input data; a controller that makes a power supply amount to the detector smaller and lowers detection sensitivity to radiation irradiation start in the detector the larger the radiation irradiation amount derived by the derivation unit; and an imaging unit that images the radiographic image after radiation irradiation start has been detected by the detector.

13 Claims, 22 Drawing Sheets

■ : RADIATION DETECTION PIXEL

FIG.10

| IMAGING TARGET SITE | EXPOSURE CONDITIONS | IRRADIATION AMOUNT |
|---|---|---|
| A | a1~a2 | X1 |
| A | a3~a4 | X2 |
| B | b1~b2 | X3 |
| B | b3~b4 | X4 |
| C | c1~c2 | X5 |
| C | c3~c4 | X6 |
| D | d1~d2 | X7 |
| D | d3~d4 | X8 |
| ⋮ | ⋮ | ⋮ |

| IRRADIATION AMOUNT | BIAS VOLTAGE |
|---|---|
| X1 | V1 |
| X2 | V2 |
| X3 | V3 |
| X4 | V4 |
| X5 | V5 |
| X6 | V6 |
| X7 | V7 |
| X8 | V8 |
| ⋮ | ⋮ |

PLEASE ENTER SUBJECT NAME,
IMAGING TARGET SITE, IMAGING POSTURE
AND EXPOSURE CONDITIONS

NAME

IMAGING
TARGET SITE

IMAGING
POSTURE

EXPOSURE      TUBE
CONDITIONS    CURRENT

TUBE
              VOLTAGE

EXPOSURE
              DURATION

INPUT
                              COMPLETE

| IRRADIATION AMOUNT | DRIVE NUMBER |
|---|---|
| X1 | N1 |
| X2 | N2 |
| X3 | N3 |
| X4 | N4 |
| X5 | N5 |
| X6 | N6 |
| X7 | N7 |
| X8 | N8 |
| ⋮ | ⋮ |

X1<X2<X3<X4<X5<X6<X7<X8
N8<N7<N6<N5<N4<N3<N2<N1

RADIOGRAPHIC IMAGING DEVICE, RADIOGRAPHIC IMAGING SYSTEM, METHOD OF CONTROLLING RADIATION DETECTION SENSITIVITY AND PROGRAM STORAGE MEDIUM

CROSS-REFERENCE TO RELATED APPLICATION

This application claims priority under 35 USC 119 from Japanese Patent Application No. 2012-158928 filed on Jul. 17, 2012, the disclosure of which is incorporated by reference herein.

BACKGROUND OF THE INVENTION

1. Field of the Invention

The present invention relates to a radiographic imaging device that captures a radiographic image expressing radiation that has passed through an imaging subject, a radiographic imaging system, a method of controlling detection sensitivity to radiation irradiation start and a storage medium stored with a program.

2. Description of the Related Art

Recently, radiation detectors such as Flat Panel Detectors (FPDs) are being implemented in which a radiation sensitive layer is disposed on a Thin Film Transistor (TFT) active matrix substrate and with which radiation can be converted directly into digital data. Radiographic imaging devices that employ such radiation detectors to capture radiographic images expressing irradiated radiation are also being implemented. Conversion methods for converting radiation into electric signals used by such radiation detectors include for example indirect conversion methods, in which radiation is first converted into light with a scintillator and then the converted light is converted into charge by a photodiode, or direct conversion methods in which radiation is converted into charge with a semiconductor layer containing for example amorphous selenium. There are various materials that may be used in the semiconductor layer for each method.

In radiographic imaging devices equipped with FPDs, it is necessary to perform synchronization control between the FPD and a radiation source in order to match the start of an accumulation operation, in which the FPD accumulates signal charge, to an irradiation timing of irradiation of radiation from the radiation source. In order to synchronize the timing for the start of radiation irradiation and the timing for the start of the accumulation operation of signal charge by the FPD, a controller such as a console that controls the radiographic imaging device receives an irradiation start signal generated by an irradiation switch connected to the radiation source and supplies this signal to the radiographic imaging device as a synchronization signal. The radiographic imaging device transitions to the accumulation operation and starts imaging on receipt of this synchronization signal.

However, in cases where an imaging system is configured including a radiographic imaging device and a radiation source, sometimes a synchronization control interface installed as standard in the radiographic imaging device or the console thereof (for example cable or connector standards, synchronization signal format) is not compatible with an interface of the radiation source. Due to such issues, radiographic imaging devices are being developed that include an automatic radiation detection function, with radiation irradiation start automatically detected by the radiographic imaging device itself, without the use of a synchronization signal.

For example, Japanese Patent Application Laid-Open (JP-A) No. 2011-185622 discloses a radiographic imaging device provided with: plural radiation detection elements arrayed in a 2D formation in each region of regions partitioned by plural scan lines and plural signal lines; current detection means that detects current flowing in a bias line for applying a bias voltage to the radiation detection elements; control means that detects radiation irradiation start based on a value of the current detected by the current detection means; and memory pre-stored with change profiles of the current detected by the current detection means during reset processing of each of the radiation detection elements. The control means detects radiation irradiation start based on a value $\Delta V$ that is the value of the current detected by the current detection means during the reset processing of each of the radiation detection elements reduced by a value corresponding to a value of the current in the change profile.

In radiographic imaging devices with automatic radiation detection functions such as those described above, since the FPD cannot be forewarned of the timing of radiation irradiation, in an irradiation standby state the power is constantly in an ON state and an alert state is maintained until radiation irradiation. There is accordingly significantly increased power consumption in comparison to techniques in which imaging is synchronized to a radiation source. In particular, portable radiographic imaging devices (electronic cassettes) are often driven by a rechargeable battery, with demand to suppress the power consumption and lengthen the operating time for each recharge. However, in radiographic imaging devices, for example, the dose of radiation irradiated onto the FPD differs, for example, according to exposure conditions such as tube current and tube voltage, and such factors as the body thickness of the imaging subject. The radiation irradiation amount irradiated onto the FPD becomes smaller for a larger body thickness of imaging subject than for a smaller body thickness, and hence a higher detection sensitivity to radiation needs to be set. However, if radiation detection sensitivity is set constantly high then, in addition to a large power consumption in the irradiation standby state, there is also concern that false detection of radiation irradiation start due to such influences as noise or vibration might occur.

SUMMARY

An aspect of the present invention provides a radiographic imaging device. The radiographic imaging device includes: a detector that detects an irradiation start of radiation irradiated during imaging of a radiographic image; a derivation unit that derives an irradiation amount of radiation that will be irradiated within a specific period of time based on input data; a controller that causes a power supply amount to the detector to become smaller and detection sensitivity to irradiation start in the detector to become lower, as the radiation irradiation amount derived by the derivation unit increases; and an imaging unit that images the radiographic image after radiation irradiation start has been detected by the detector.

BRIEF DESCRIPTION OF THE DRAWINGS

Exemplary embodiments of the present invention will be described in detail based on the following figures, wherein:

FIG. 10 is a diagram illustrating a first reference table according to an exemplary embodiment of the present invention;

FIG. 11 is a diagram illustrating a second reference table according to an exemplary embodiment of the present invention;

FIG. 13 is a schematic diagram illustrating an example of an initial information input screen according to an exemplary embodiment of the present invention;

DETAILED DESCRIPTION

First Exemplary Embodiment

Figure 1:
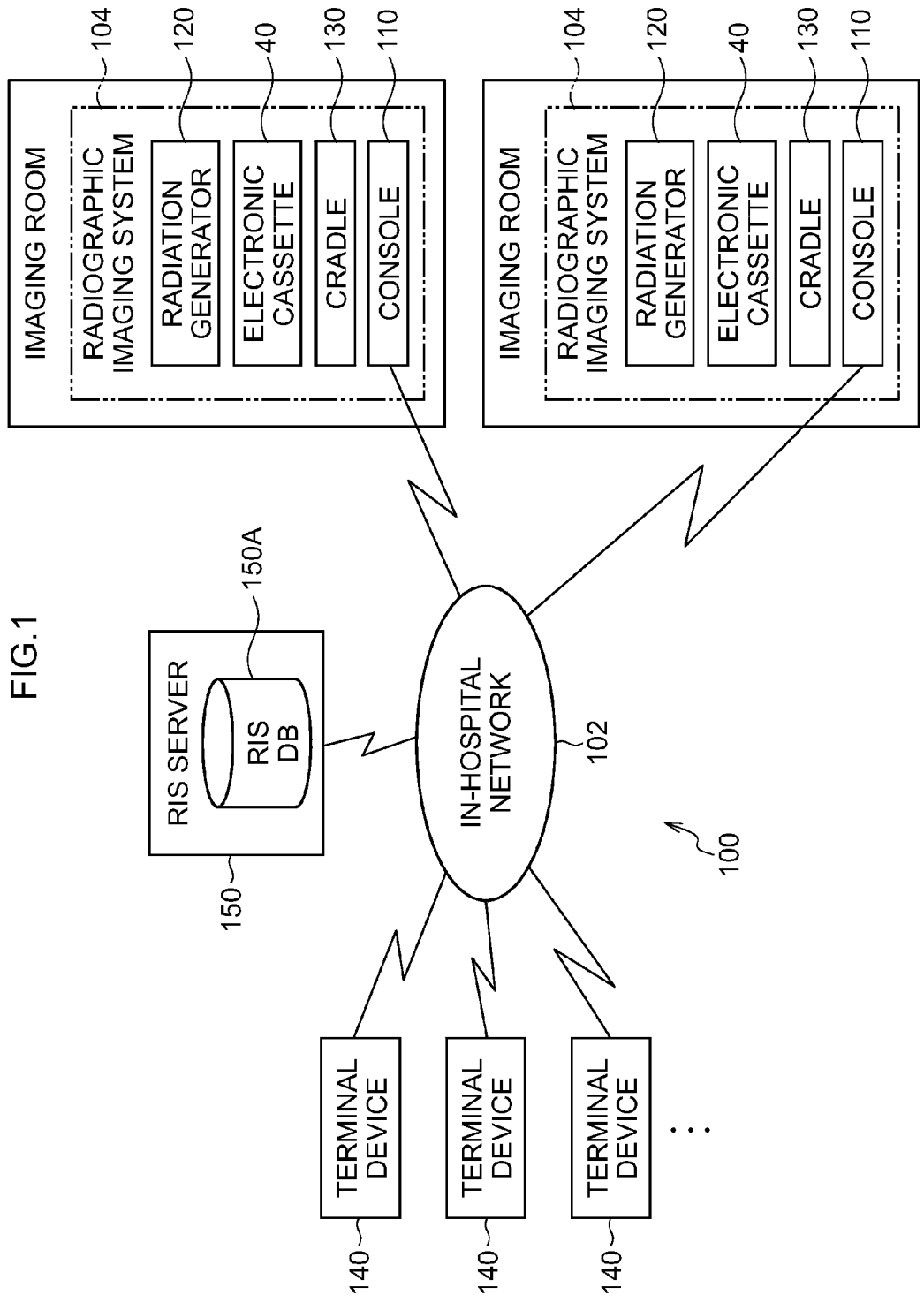
FIG. 1 is a block diagram illustrating a configuration of a radiology information system according to an exemplary embodiment of the present invention.

Detailed explanation follows regarding an exemplary embodiment of the present invention, with reference to the drawings. Note that in the following explanation, an example is used of a case in which the present invention is applied to a radiology information system that is a system that performs comprehensive management of data used in a hospital radiology department. Moreover, substantially the same or equivalent configuration elements or portions are appended with the same reference numerals in each of the drawings.

FIG. 1 illustrates a configuration of a radiology information system (referred to below as "RIS") 100 according to an exemplary embodiment of the present invention.

The RIS 100 is a system for managing information such as medical appointments and diagnostic records in a radiology department and configures part of a hospital information system (referred to below as "HIS").

The RIS 100 includes plural imaging request terminal devices 140 (referred to below as "terminal devices"), an RIS server 150, and radiographic imaging systems (referred to below as "imaging systems") 104. The imaging systems are installed in individual radiographic imaging rooms (or operating rooms) in a hospital. The RIS 100 is configured by the terminal devices 140, the RIS server 150. The imaging systems 104 are respectively connected to an in-hospital network 102 configured by for example a wired or wireless local area network (LAN). The RIS 100 configures part of the HIS disposed in the same hospital, and an HIS server that manages the HIS overall is also connected to the in-hospital network 102.

The terminal devices 140 are for doctors or radiographers to input and browse diagnostic information and facility reservations, and to make radiographic imaging requests and imaging reservations. Each of the terminal devices 140 includes a personal computer with a display device, and the terminal devices 140 are connected so as to be capable of communicating with each other through the RIS server 150 and the in-hospital network 102.

The RIS server 150 receives imaging requests from each of the terminal devices 140 and manages radiographic imaging schedules in the imaging systems 104. The RIS server 150 is configured including a database 150A.

The database 150A is configured including: data relating to patients (imaging subjects), such as patient attribute information (for example name, sex, date of birth, age, blood type, body weight, patient identification (ID)), medical history, consultation history, and previously captured radiographic images; data relating to electronic cassettes 40, described later, that are used in the imaging systems 104, such as identification number (ID data), model, size, sensitivity, date of first use, and numbers of times used; and environment data representing the environment in which radiographic images are captured using the electronic cassettes 40, namely the environment in which the electronic cassettes 40 are used (for example radiographic imaging room, operating room).

A doctor or radiographer operates the imaging systems 104 to perform radiographic imaging in response to an instruction from the RIS server 150. Each of the imaging systems 104 is equipped with a radiation generator 120 that irradiates the patient (imaging subject) with an amount of radiation X such as X-rays (see also FIG. 7) from a radiation source 121 (see also FIG. 9) according to exposure conditions. Each of the imaging systems 104 is also provided with the electronic cassettes 40, each of which have a built-in radiation detector 20 (see also FIG. 7) that absorbs the radiation X that has passed through an imaging target site of the patient (imaging subject) and generates charge, and generates image data expressing a radiographic image based on the amount of generated charge. The imaging systems 104 are also provided with a cradle 130 that is built into the electronic cassette 40 and charges a battery, and a console 110 that controls the electronic cassette 40 and the radiation generator 120.

The console 110 acquires various types of data included in the database 150A from the RIS server 150, stores the data in a HDD 116, described later, (see FIG. 9), and uses the data as needed to control the electronic cassette 40 and the radiation generator 120.

Figure 2:
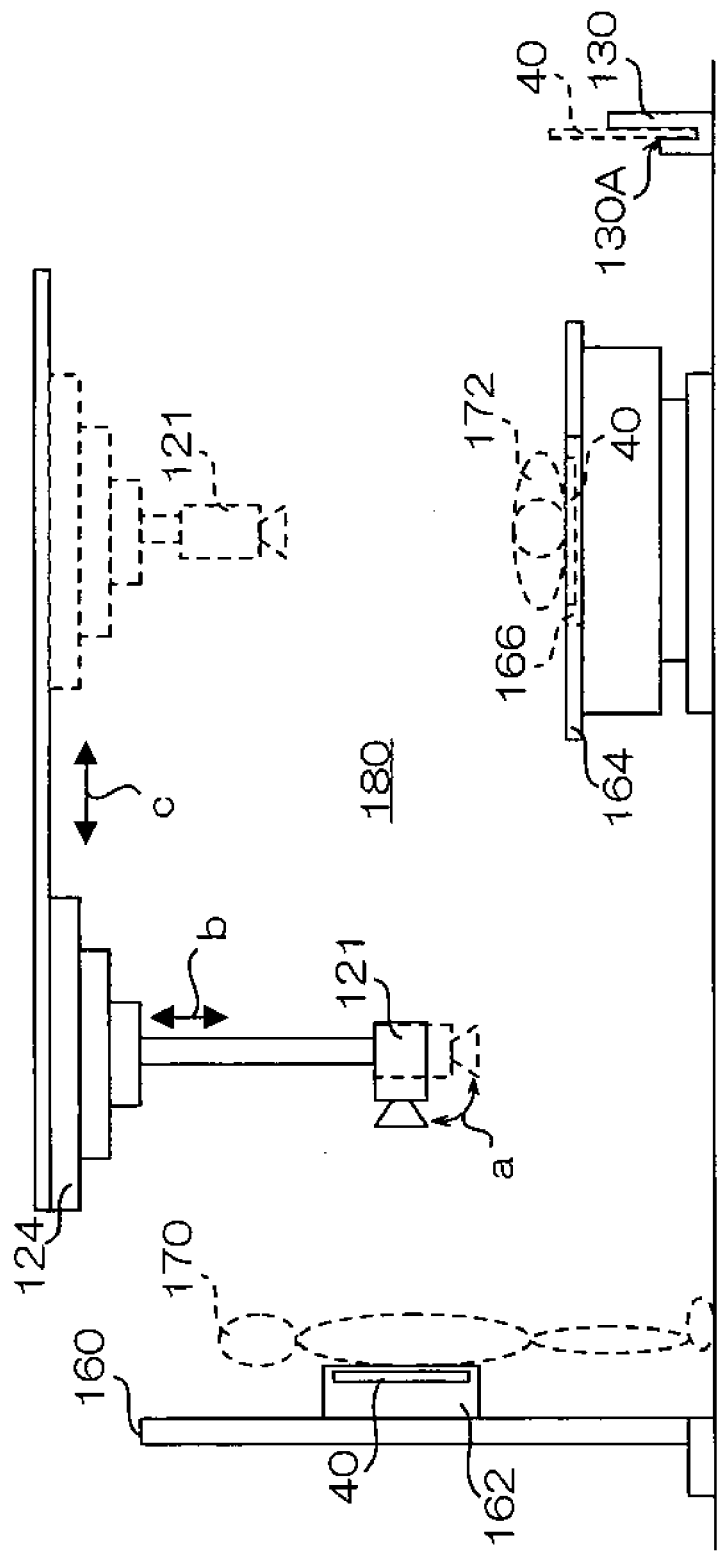
FIG. 2 is a side view illustrating an example of an installed state of each device of a radiographic imaging system according to an exemplary embodiment of the present invention in a radiographic imaging room.

FIG. 2 shows an example of an installed state of each of the devices configuring the imaging system 104 of an exemplary embodiment of the present invention in a radiographic imaging room 180.

As shown in FIG. 2, an upright stand 160 employed when performing radiographic imaging in a standing position, and a prone table 164 employed when performing radiographic imaging in a prone position, are installed in the radiographic imaging room 180. The space in front of the upright stand 160 serves as a patient (imaging subject) imaging position 170 when performing radiographic imaging in a standing position. The space above the prone table 164 serves as a patient (imaging subject) imaging position 172 when performing radiographic imaging in a prone position.

A holder 162 that holds the electronic cassette 40 is provided to the upright stand 160. The electronic cassette 40 is held by the holder 162 when capturing a radiographic image in the standing position. Similarly, a holder 166 that holds the electronic cassette 40 is provided to the prone table 164. The electronic cassette 40 is held by the holder 166 when capturing a radiographic image in the prone position.

Further, a supporting and moving mechanism 124 is disposed in the radiographic imaging room 180. The supporting and moving mechanism 124 supports the radiation source 121 in such a way that the radiation source 121 is rotatable about a horizontal axis (the direction of arrow a in FIG. 2), is movable in a vertical direction (the direction of arrow b in FIG. 2), and is movable in a horizontal direction (the direction of arrow c in FIG. 2). It is accordingly possible to employ the single radiation source 121 to perform radiographic imaging in a standing position and in a prone position.

The cradle 130 includes a housing portion 130A capable of housing the electronic cassette 40. When not in use, the electronic cassette 40 is housed in the housing portion 130A of the cradle 130, and the built-in battery of the electronic cassette 40 is charged with the electronic cassette 40 in a housed state in the housing portion 130A of the cradle 130.

In the imaging system 104, various types of data are transmitted and received by wireless communication between the radiation generator 120 and the console 110 and between the electronic cassette 40 and the console 110.

The electronic cassette 40 is not limited to being used only in a state held by the holder 162 of the upright stand 160 or the holder 166 of the prone table 164. Due to its portability the electronic cassette 40 may also be employed in a state not held by a holder, for example when imaging arm or leg regions.

Figure 3:
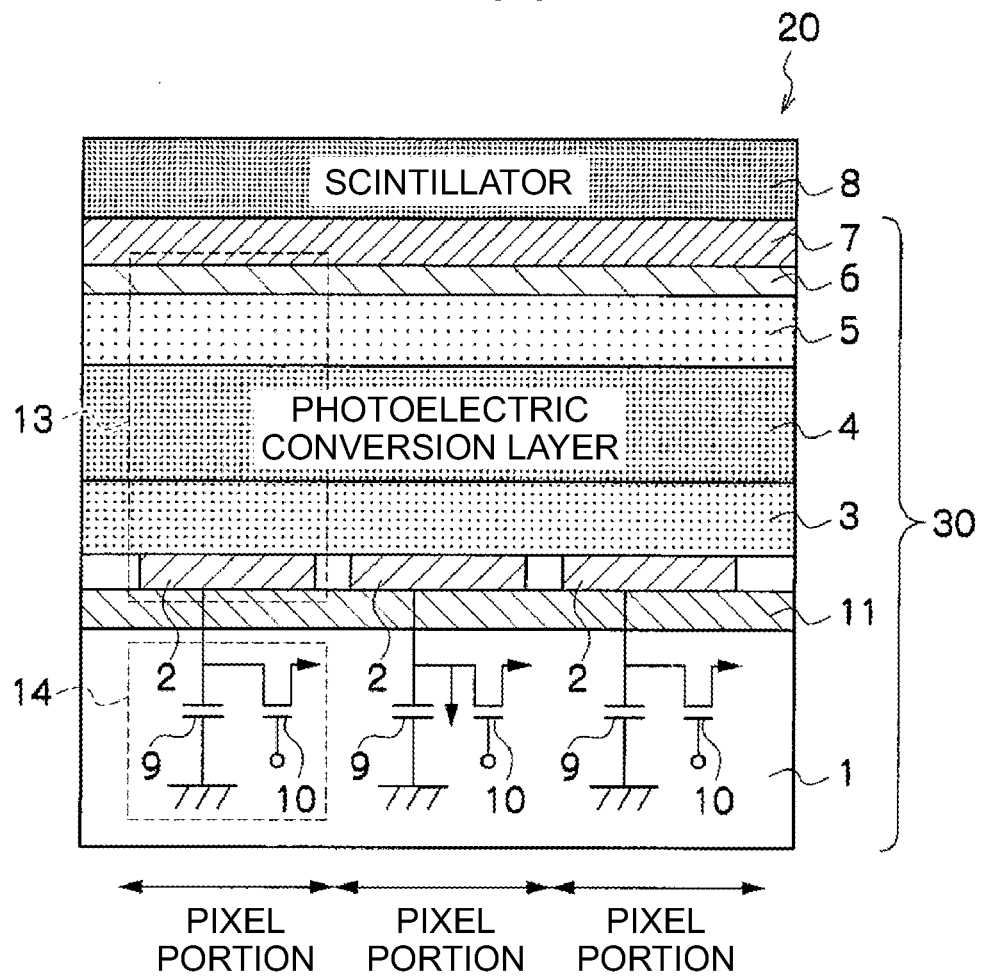
FIG. 3 is a cross-section illustrating a schematic configuration of a radiation detector according to an exemplary embodiment of the present invention.

Explanation follows regarding the configuration of the radiation detector 20 that is built into the electronic cassette 40. FIG. 3 is a cross-section schematically illustrating the configuration of a portion including three pixels of the radiation detector 20 of an exemplary embodiment of the present invention.

As shown in FIG. 3, the radiation detector 20 is configured by forming a TFT substrate 30 by forming signal output portions 14, sensor portions 13 and a transparent insulating film 7 in sequence on a substrate 1, and adhering a scintillator 8 to the TFT substrate 30 using for example an adhesive resin with low light absorbance characteristics. A pixel is configured by each of the signal output portions 14 and each of the sensor portions 13.

The scintillator 8 is formed on the sensor portions 13 with the transparent insulating film 7 interposed therebetween. The scintillator 8 includes a phosphor that converts incident radiation into light and emits the light. Namely, the scintillator 8 absorbs radiation that has passed through the patient (imaging subject) and emits light.

The wavelength region of the light emitted by the scintillator 8 is preferably in the visible light range (wavelengths of 360 nm to 830 nm). The wavelength region of the light emitted by the scintillator 8 more preferably includes the green wavelength region in order to enable monochrome imaging by the radiation detector 20.

A phosphor including cesium iodide (CsI) is preferably employed as the phosphor in the scintillator 8 in a case in which imaging employs X-rays for the radiation. CsI(Tl) (thallium-doped cesium iodide) with a light emission spectrum of 420 nm to 700 nm when X-rays are applied is particularly preferably employed. The emission peak wavelength in the visible light range of CsI(Tl) is 565 nm.

The sensor portions 13 are each configured including an upper electrode 6, a lower electrode 2, and a photoelectric conversion layer 4 that is provided between the upper electrode 6 and the lower electrode 2. The photoelectric conversion layer 4 is configured by an organic photoelectric conversion material that absorbs the light emitted by the scintillator 8 and generates charge.

The upper electrode 6 is preferably configured from a conducting material that is transparent at least with respect to the light emission wavelength of the scintillator 8 since it is necessary to allow the light produced by the scintillator 8 to be incident to the photoelectric conversion layer 4. Specifically, a transparent conducting oxide (TCO) is preferably employed that has high transmittance with respect to visible light and has a small resistance value. A metal thin film of Au or the like can also be used as the upper electrode 6, however TCO is more preferable since the resistance value increases readily when trying to obtain a transmittance of 90% or more. For example, ITO, IZO, AZO, FTO, $SnO_2$, $TiO_2$, and $ZnO_2$ can be preferably used, with ITO being the most preferred from the perspectives of ease of processing, low resistance, and transparency. The upper electrode 6 may be configured from a single sheet common to all the pixels or may be divided per pixel.

The photoelectric conversion layer 4 includes an organic photoelectric conversion material, absorbs the light emitted from the scintillator 8, and generates charge corresponding to the amount of light absorbed. The photoelectric conversion layer 4 including the organic photoelectric conversion material has a sharp absorption spectrum in the visible range, and virtually no electromagnetic waves are absorbed by the photoelectric conversion layer 4 other than the light emitted by the scintillator 8. Noise generated as a result of radiation such as X-rays being absorbed by the photoelectric conversion layer 4 can accordingly be effectively suppressed.

The absorption peak wavelength of the organic photoelectric conversion material configuring the photoelectric conversion layer 4 is preferably as close as possible to the emission peak wavelength of the scintillator 8 in order for the organic photoelectric conversion material to most efficiently absorb the light emitted by the scintillator 8. Ideally, the absorption peak wavelength of the organic photoelectric conversion material matches the emission peak wavelength of the scintillator 8. However as long as the difference between the two is small, the organic photoelectric conversion material can adequately absorb the light emitted from the scintillator 8. Specifically, the difference between the absorption peak wavelength of the organic photoelectric conversion material and the emission peak wavelength of the scintillator 8 with respect to radiation is preferably 10 nm or below. The difference is even more preferably 5 nm or below.

Examples of organic photoelectric conversion materials that can satisfy this condition include quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material for the scintillator 8, it is possible to make the difference between the peak wavelengths 5 nm or below, and the amount of charge generated in the photoelectric conversion layer 4 can be substantially maximized.

Figure 4:
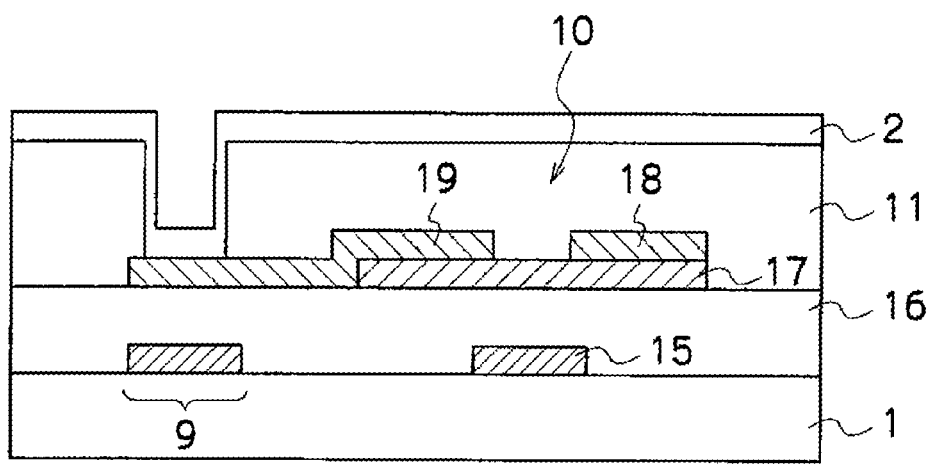
FIG. 4 is a cross-section schematically illustrating a configuration of a signal output portion of a radiation detector according to an exemplary embodiment of the present invention.

The signal output portions 14 are formed on the surface of the substrate 1 below the lower electrodes 2. FIG. 4 schematically illustrates the configuration of one of the signal output portions 14.

As shown in FIG. 4, each of the signal output portions 14 include a capacitor 9 and a field-effect thin film transistor (TFT: also referred to below simply as a "thin film transistor") 10. The capacitor 9 accumulates charge that has moved to the lower electrode 2. The thin film transistor 10 reads out the charge accumulated in the capacitor 9 into signal lines 36, described later (see FIG. 5). The capacitor 9 and the thin film transistor 10 are disposed so as to overlap with the lower electrode 2 in plan view. Namely, the signal output portion 14 and the sensor portion 13 overlap in the thickness direction in each of the pixels. In order to reduce the surface area of the radiation detector 20 (pixels), it is desirable for the region in which the capacitor 9 and the thin film transistor 10 are formed to be completely covered by the lower electrode 2.

The capacitor 9 is electrically connected to the corresponding lower electrode 2 through a wire of a conductive material that is formed penetrating an insulating film 11 disposed between the substrate 1 and the lower electrode 2. Charge collected in the lower electrode 2 can accordingly be moved to the capacitor 9.

A gate electrode 15, a gate insulating film 16, and an active layer (channel layer) 17 are stacked in the thin film transistor 10. A source electrode 18 and a drain electrode 19 are formed at a specific separation from each other on the active layer 17.

The active layer 17 may, for example, be formed by a material such as amorphous silicon, an amorphous oxide, an organic semiconductor material or carbon nanotubes. Note that the material configuring the active layer 17 is not limited to the above.

As examples of amorphous oxides that may be used to configure the active layer 17, oxides including at least one of In, Ga, and Zn (for example In—O amorphous oxides) are preferable, oxides including at least two of In, Ga, and Zn (for example In—Zn—O amorphous oxides, In—Ga—O amorphous oxides, or Ga—Zn—O amorphous oxides) are more preferable, and oxides including In, Ga, and Zn are particularly preferable. As an In—Ga—Zn—O amorphous oxide, an amorphous oxide whose composition in a crystalline state is expressed by $InGaO_3(ZnO)_m$ (where m is a natural number less than 6) is preferable, with $InGaZnO_4$ being more preferable.

Examples of organic semiconductor materials capable of configuring the active layer 17 include phthalocyanine compounds, pentacene, and vanadyl phthalocyanine, however there is no limitation thereto. Configurations of phthalocyanine compounds are described in detail in JP-A No. 2009-212389, so descriptions thereof will be omitted here.

By forming the active layer 17 of the thin film transistor 10 from an amorphous oxide, an organic semiconductor material, or carbon nanotubes, the active layer 17 does not absorb radiation such as X-rays, or this is restricted to an extremely minute amount if radiation is absorbed, so the generation of noise in the signal output portion 14 can be effectively suppressed.

Further, in a case in which the active layer 17 is formed with carbon nanotubes, the switching speed of the thin film transistor 10 can be increased, and the thin film transistor 10 can be formed having a low degree of absorption of light in the visible light range. In a case in which the active layer 17 is formed with carbon nanotubes, the performance of the thin film transistor 10 drops significantly if even a tiny amount of metal impurity is incorporated into the active layer 17, so it is necessary to separate, extract, and form extremely high-purity carbon nanotubes using centrifugal separation or the like.

Here, the amorphous oxide, organic semiconductor material, or carbon nanotubes configuring the active layer 17 of the thin film transistor 10 and the organic photoelectric conversion material configuring the photoelectric conversion layer 4 are all capable of being formed into films at a low temperature. Consequently, the substrate 1 is not limited to a substrate with high heat resistance, such as a semiconductor substrate, a quartz substrate, or a glass substrate, and a flexible substrate, such as plastic, with aramid or bionanofibers can also be used. Specific flexible substrates that can be used include polyesters, such as polyethylene terephthalate, polybutylene phthalate and polyethylene naphthalate, polystyrene, polycarbonate, polyethersulphone, polyarylate, polyimide, polycyclic olefin, norbornene resin, and poly(chloro-trifluoro-ethylene). Employing a flexible substrate made of plastic can achieve a reduction in weight, which is advantageous from the perspective of for example portability.

Further, for example an insulating layer for ensuring insulation, a gas barrier layer for preventing the transmission of moisture and/or oxygen, and an undercoat layer for improving flatness or adhesion to the electrodes, may also be disposed on the substrate 1.

High-temperature processes of 200 degrees or higher can be applied to aramids, so a transparent electrode material can be cured at a high temperature and given a low resistance, and aramids are also compatible with automatic packaging of driver ICs including solder reflow processes. Aramids also have a thermal expansion coefficient that is close to that of indium tin oxide (ITO) or a glass substrate, so they have little warping after manufacture and do not break easily. Further, aramids can also form a thinner substrate compared to a glass substrate or the like. An ultrathin glass substrate and an aramid may also be stacked to form a substrate.

Further, bionanofibers are composites of cellulose microfibril bundles (bacterial cellulose) produced by a bacterium (*Acetobacter xylinum*) and a transparent resin. Cellulose microfibril bundles have a width of 50 nm, which is a size that is 1/10 visible wavelengths, and have high strength, high elasticity, and low thermal expansion. By impregnating and hardening a transparent resin such as an acrylic resin or an epoxy resin in bacterial cellulose, bionanofibers can be obtained that exhibit a light transmittance of about 90% at a wavelength of 500 nm while including fibers at 60 to 70%. Bionanofibers have a low thermal expansion coefficient (3 to 7 ppm) comparable to silicon crystal, a strength comparable to steel (460 MPa), high elasticity (30 GPa), and are flexible, thereby enabling the substrate 1 to be formed thinner compared for example to a glass substrate.

Figure 5:
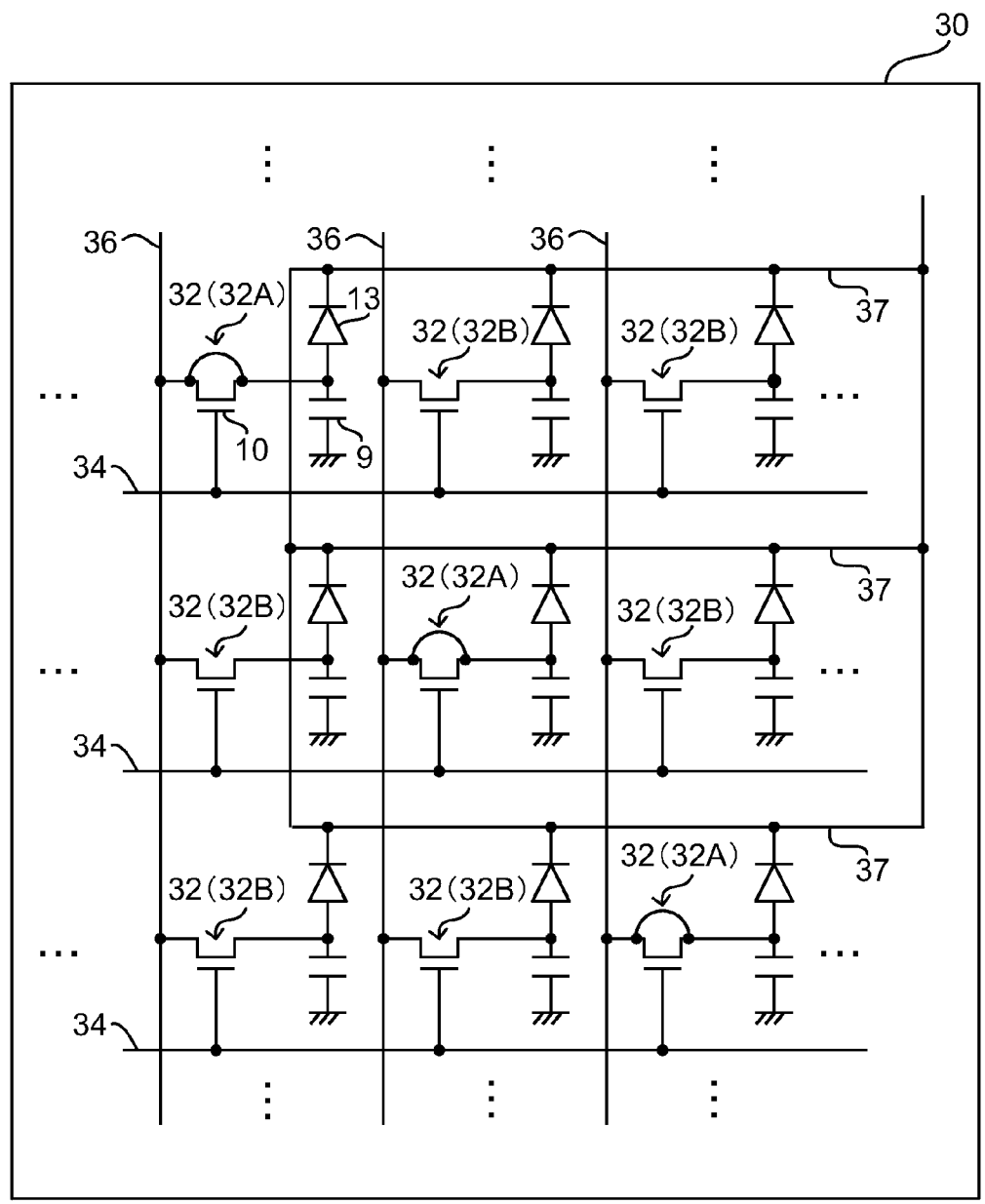
FIG. 5 is a diagram illustrating a configuration of a TFT substrate according to an exemplary embodiment of the present invention.

FIG. 5 is a plan view illustrating a configuration of the TFT substrate 30 configuring the radiation detector 20. As shown in FIG. 5, plural pixels 32 each configured including the sensor portion 13, the capacitor 9, and the thin film transistor 10 are disposed on the TFT substrate 30 in a two-dimensional pattern in one direction (the row direction in FIG. 5) and an direction intersecting the one direction (the column direction in FIG. 5).

The TFT substrate 30 is disposed with plural gate lines 34 that extend in the one direction (the row direction) and that switch each of the thin film transistors 100N and OFF, and the plural signal lines 36 that extend in the intersecting direction (the column direction) and that read the charges through the thin film transistors 10 that are in an ON state.

Moreover, the respective sensor portions 13 are connected to bias lines 37. The bias lines 37 are connected to a bias voltage generator 71, described later. A bias voltage is supplied from the bias voltage generator 71 through the bias lines 37 to each of the sensor portions 13.

The TFT substrate 30 is formed in flat plate shape, and in a quadrilateral shape having four sides on its outer edges in plan view. More specifically, the TFT substrate 30 is formed in a rectangular shape.

The TFT substrate 30 includes pixels 32 that are employed to detect the presence or absence of radiation irradiation, and pixels 32 that capture a radiographic image. In the following explanation, the pixels 32 that detect radiation will be referred to as radiation detection pixels 32A, and the remaining pixels 32 will be referred to as radiographic imaging pixels 32B. In the electronic cassette 40 of the present exemplary embodiment, the start of radiation irradiation is detected using the radiation detection pixels 32A.

As illustrated in FIG. 5, the sources and drains of the thin film transistors 10 are shorted in the radiation detection pixels 32A. Accordingly, in the radiation detection pixels 32A the charge accumulated in the capacitors 9 flows out into the signal lines 36 irrespective of the switching state of the thin film transistors 10.

Figure 6:
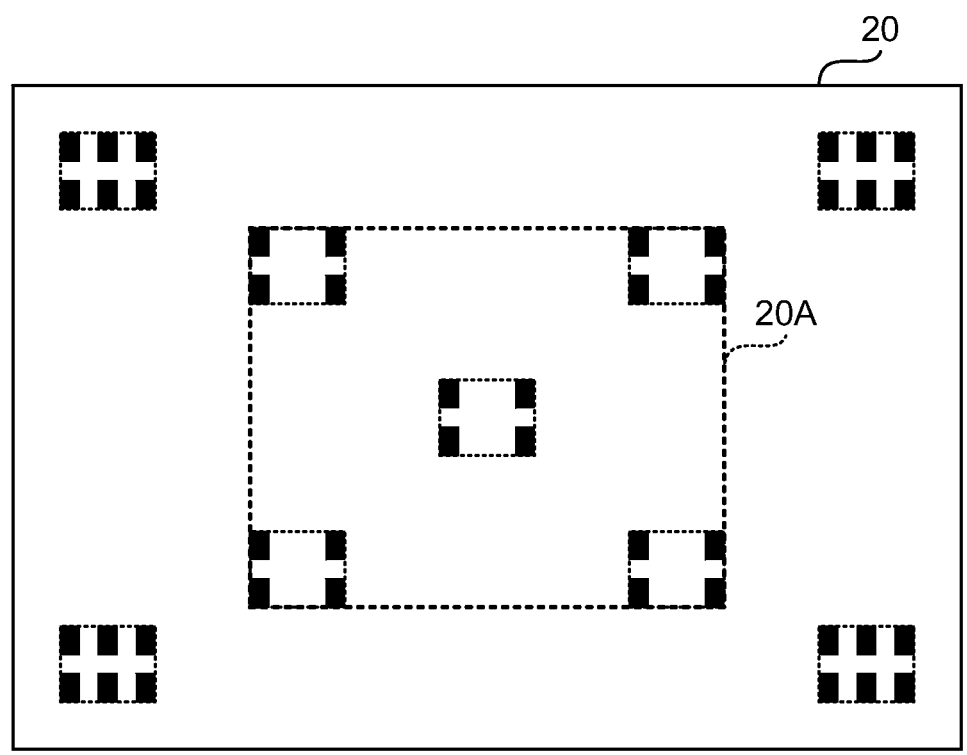
FIG. 6 is a plan view illustrating the disposal of radiation detection pixels according to an exemplary embodiment of the present invention.

Note that the radiation detection pixels 32A may be disposed with uniform distribution on the TFT substrate 30. Moreover, as shown in the example in FIG. 6, the radiation detection pixels 32A may be disposed at a comparatively low density in a partial region (a rectangular region centered on a central portion of an imaging region of the radiation detector 20 in the present exemplary embodiment) 20A that includes the central portion of the imaging region, and disposed at a comparatively high density at regions peripheral thereto.

In the TFT substrate 30, it is not possible to obtain radiographic image pixel data for the positions where the radiation detection pixels 32A are disposed within the imaging region. Accordingly, in the TFT substrate 30 the radiation detection pixels 32A are disposed so as to be dispersed within the imaging region, and missing pixel correction processing is executed by the console 110 to interpolate radiographic image pixel data for the positions where the radiation detection pixels 32A are disposed, by employing pixel data obtained from the radiographic imaging pixels 32B positioned peripherally to the radiation detection pixels 32A.

Figure 7:
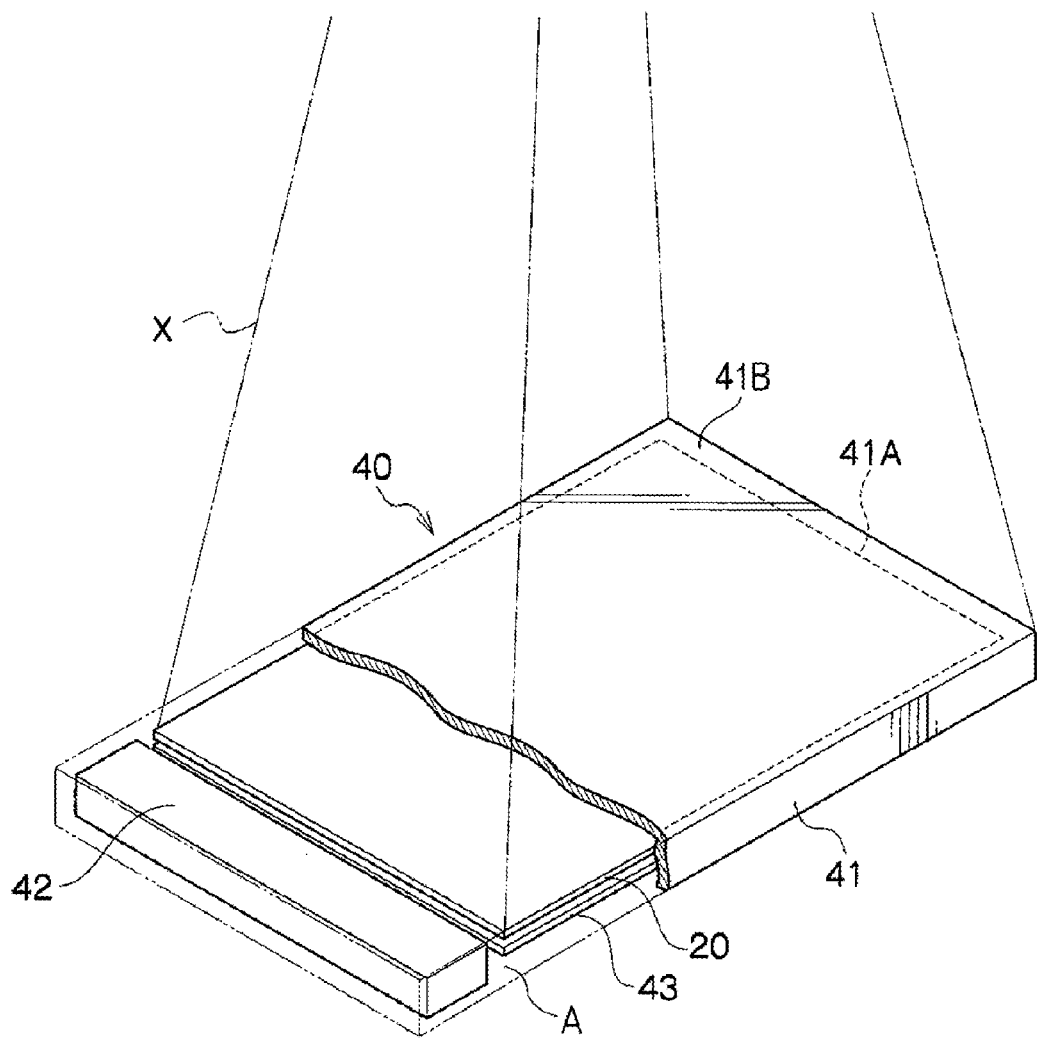
FIG. 7 is a perspective view illustrating a configuration of an electronic cassette according to an exemplary embodiment of the present invention.

Explanation next follows regarding the configuration of the electronic cassette 40 according to the present exemplary embodiment. FIG. 7 is a perspective view illustrating a configuration of the electronic cassette 40 of an exemplary embodiment of the present invention.

As shown in FIG. 7, the electronic cassette 40 is equipped with a housing 41 that is formed from a material that allows radiation to pass through, and the electronic cassette 40 is configured with a waterproof and airtight structure. There is a concern that blood or other contaminants may adhere to the electronic cassette 40 when the electronic cassette 40 is used for example in an operating room. Therefore, giving the electronic cassette 40 a waterproof and airtight structure enables a single electronic cassette 40 to be used repeatedly by disinfecting the electronic cassette 40 as required.

A space A that accommodates various components is formed inside the housing 41. The radiation detector 20 that detects the radiation X that has passed through the patient (imaging subject), and a lead plate 43 that absorbs backscattered rays of the radiation X, are disposed inside the space A in this order from an irradiated face side of the housing 41 that is irradiated with the radiation X.

A region corresponding to the placement position of the radiation detector 20 configures an imaging region 41A that is capable of detecting the radiation. The face of the housing 41 with the imaging region 41A is configured as a top plate 41B of the electronic cassette 40. In the electronic cassette 40 of the present exemplary embodiment, the radiation detector 20 is disposed so that the TFT substrate 30 is on the top plate 41B side, and in the housing 41 the TFT substrate 30 is adhered to the inside face of the top plate 41B (the face of the top plate 41B at the opposite side of the face to which radiation is incident).

As shown in FIG. 7, a case 42 that accommodates a cassette controller 58, described later, and a power source unit 70 (see FIG. 9 for both), is placed at one end side of the interior of the housing 41 at a position that does not overlap with the radiation detector 20 (outside the range of the imaging region 41A).

The housing 41 is for example configured from carbon fiber, aluminum, magnesium, bionanofibers (cellulose microfibrils), or a composite material, in order to achieve a reduction in weight for the electronic cassette 40 overall.

As a composite material, for example, a material including a reinforcement fiber resin is used, with for example carbon or cellulose incorporated in the reinforcement fiber resin. Specific examples of composite materials that may be used include carbon fiber reinforced plastic (CFRP), a composite material with a structure where a foam material is sandwiched by CFRP, or a composite material in which the surface of a foam material is coated with CFRP. In the present exemplary embodiment, a composite material with a structure in which a foam material is sandwiched by CFRP is used. The strength (rigidity) of the housing 41 can accordingly be raised compared to a case in which the housing 41 is configured by a carbon element.

Figure 8:
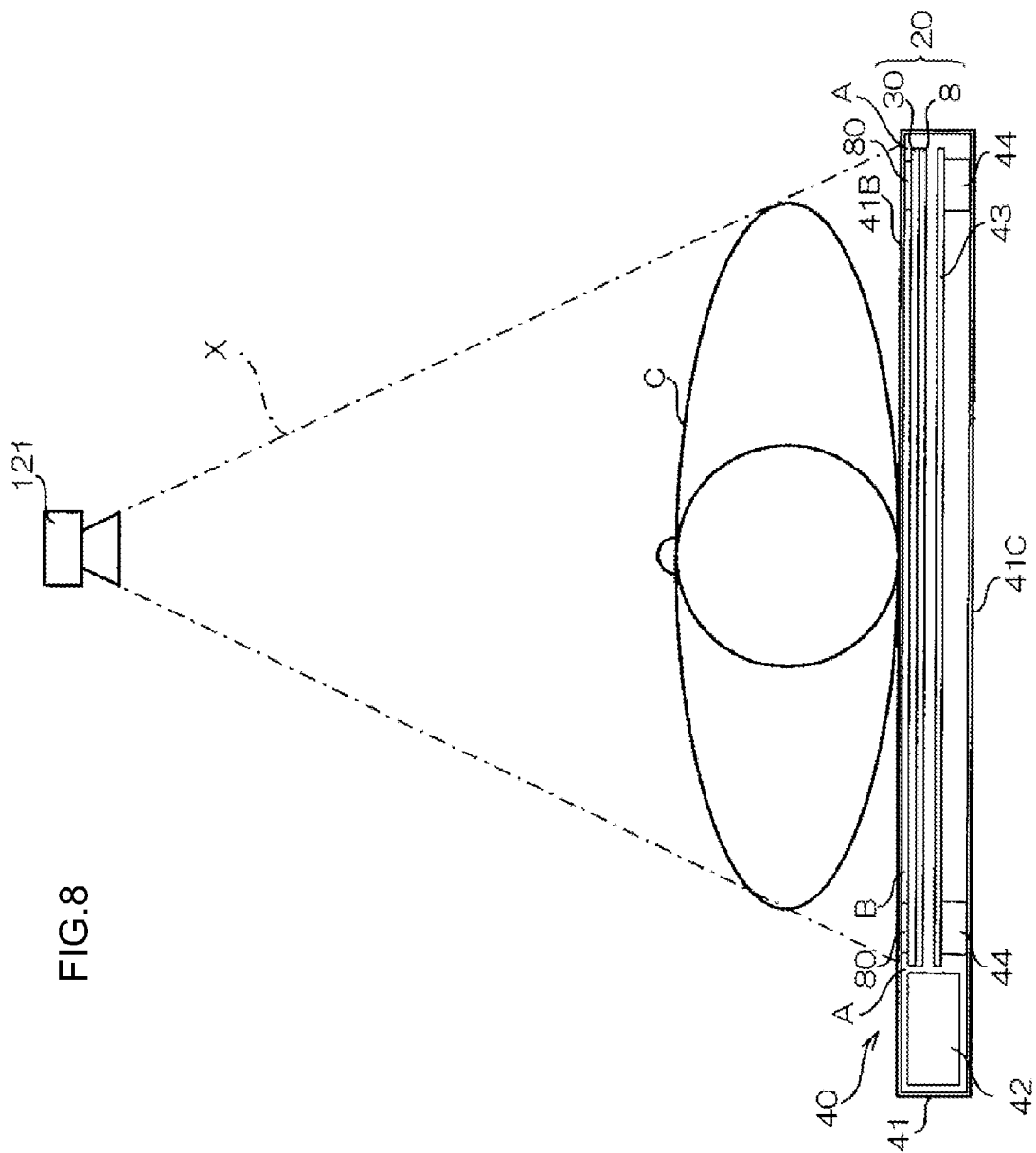
FIG. 8 is a cross-section illustrating a configuration of an electronic cassette according to an exemplary embodiment of the present invention.

FIG. 8 is a cross-section illustrating a configuration of the electronic cassette 40. As shown in FIG. 8, support members 44 are disposed inside the housing 41 on the inner face of a back face portion 41C that faces the top plate 41B. The radiation detector 20 and the lead plate 43 are arrayed in this order along the radiation X application direction between the support members 44 and the top plate 41B. The support members 44 support the lead plate 43 and, from the perspective of weight reduction and the perspective of absorbing dimensional deviation, are configured by for example a foam material.

As shown in FIG. 8, adhesive members 80 are provided at the inner face of the top plate 41B to detachably adhere the TFT substrate 30 of the radiation detector 20. Double-sided tape, for example, can be employed for the adhesive members 80. In this case, the double-sided tape is formed in such a way that the adhesive force of one adhesive face is stronger than that of the other adhesive face.

Specifically, the face with the weaker adhesive force (weak adhesive face) is set to have a 180-degree peel strength of 1.0 N/cm or lower. The face with the stronger adhesive force (strong adhesive face) contacts the top plate 41B, and the weaker adhesive face contacts the TFT substrate 30. The thickness of the electronic cassette 40 can accordingly be made thinner than in a case in which the radiation detector 20 is fixed to the top plate 41B by, for example, fixing members such as screws. Moreover, even if the top plate 41B deforms under impact or load, the radiation detector 20 follows the deformation of the top plate 41B that has high rigidity, so only deformation of large radius of curvature (a gentle curve) arises, reducing the likelihood of the radiation detector 20 sustaining damage due to localized deformation of low radius of curvature. Moreover, the radiation detector 20 contributes to raising the rigidity of the top plate 41B.

Thus in the electronic cassette 40 according to the present exemplary embodiment, since the radiation detector 20 is adhered at the inside of the top plate 41B of the housing 41, the housing 41 is separable into two between the top plate 41B side and the back face portion 41C side. The housing 41 is placed in a state divided into the two parts of the top plate 41B side and the back face portion 41C side in order to adhere the radiation detector 20 to the top plate 41B or detach the radiation detector 20 from the top plate 41B.

In the present exemplary embodiment, adhering the radiation detector 20 to the top plate 41B does not have to be performed for example in a clean room. This is due to the fact that even if foreign objects such as metal fragments that absorb radiation where to be incorporated between the radiation detector 20 and the top plate 41B, such foreign objects can be removed by detaching the radiation detector 20 from the top plate 41B.

Figure 9:
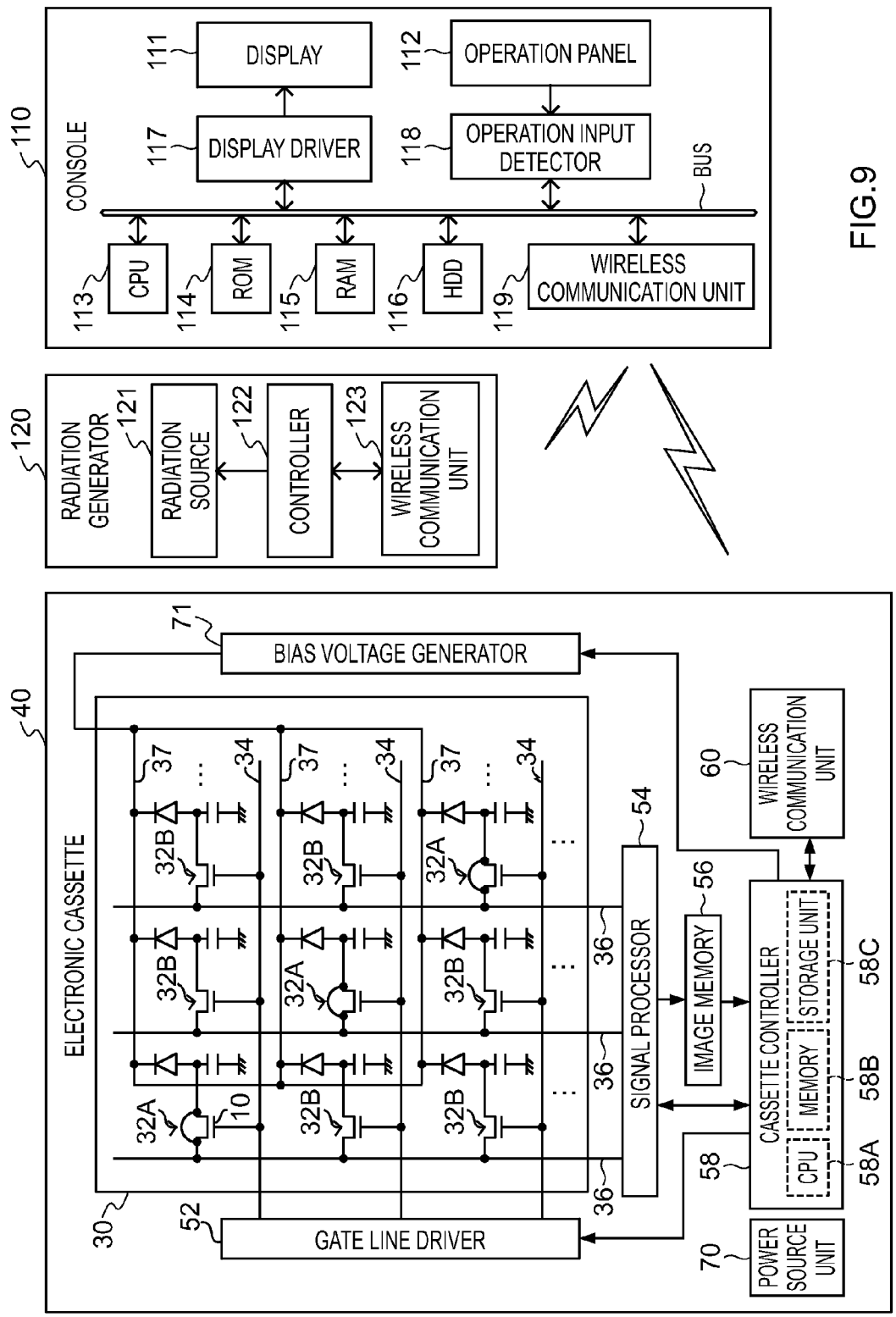
FIG. 9 is a block diagram illustrating a configuration of relevant portions of an electrical system of a radiographic imaging system according to an exemplary embodiment of the present invention.

FIG. 9 is a drawing illustrating a configuration of relevant portions of an electrical system of the imaging system 104 of the present exemplary embodiment. As shown in FIG. 9, in the TFT substrate 30 configuring the radiation detector 20 built into the electronic cassette 40, a gate line driver 52 is disposed on one side of two adjacent sides, and a signal processor 54 is disposed on the other side. The individual gate lines 34 of the TFT substrate 30 configuring the radiation detector 20 are connected to the gate line driver 52, and the individual signal lines 36 of the TFT substrate 30 are connected to the signal processor 54.

An image memory 56, the cassette controller 58, a wireless communication unit 60, the power source unit 70 and a bias voltage generator 71 are provided inside the housing 41.

Each of the thin film transistors 10 of the TFT substrate 30 are switched ON in sequence in row units by signals supplied through the gate lines 34 from the gate line driver 52, and the charges that have been read out by the thin film transistors 10 being switched to an ON state are transmitted through the signal lines 36 as electric signals and input to the signal processor 54. The charges are thereby read out in sequence by row unit, and a two-dimensional radiographic image is acquired.

The signal processor 54 is configured including charge amplifiers, sample-and-hold circuits, a multiplexer and an analogue-to-digital (A/D) converter. The charge amplifiers generate electric signals with a voltage level corresponding to the amount of charge read out from the sensor portions 13 through each of the signal lines 36. The signal levels of the electric signals generated by the charge amplifiers are held by the sample-and-hold circuits. Output terminals of the sample-and-hold circuits are connected to the common multiplexer. The multiplexer converts the signal levels held by the sample-and-hold circuits into serial data and supplies this serial data to the A/D converter. The A/D converter converts the analogue electric signals supplied from the multiplexer into image data as digital signals.

The image memory 56 is connected to the signal processor 54. The image data output from the A/D converter of the signal processor 54 are sequentially stored in the image memory 56. The image memory 56 has a storage capacity that is capable of storing a predetermined number of frames' worth of image data. The image data obtained by the imaging are sequentially stored in the image memory 56 each time radiographic imaging is performed. The image memory 56 is also connected to the cassette controller 58.

The bias voltage from the bias voltage generator 71 is applied through the bias lines 37 to the sensor portions 13. The sensor portions 13 generate more charge the greater the value of the bias voltage applied. Namely, the detection sensitivity to radiation rises the greater the value of the bias voltage applied to the sensor portions 13. The bias voltage generator 71 is a variable voltage source in which the output voltage is variable, and a bias voltage of a voltage level corresponding to a control signal applied from a cassette controller 58, described later, is supplied to the sensor portions 13. Namely, the detection sensitivity to radiation of the sensor portions 13 is controlled by the cassette controller 58.

The cassette controller 58 performs comprehensive control of the operation of the overall electronic cassette 40 including output voltage control of the bias voltage generator 71 described above. The cassette controller 58 is configured including a microcomputer, and is equipped with a central processing unit (CPU) 58A, a memory 58B including read-only memory (ROM) and random access memory (RAM), and a nonvolatile storage unit 58C configured for example by flash memory. The wireless communication unit 60 is connected to the cassette controller 58.

The wireless communication unit 60 conforms to a wireless local area network (LAN) standard such as typified by the Institute of Electrical and Electronics Engineers (IEEE) 802.11a/b/g and controls the transmission of various types of data to and from external devices by wireless communication. Through the wireless communication unit 60, the cassette controller 58 enabled for wireless communication with external devices such as the console 110 that performs control relating to radiographic imaging and is enabled for transmitting and receiving various types of data to and from the console 110, for example. Imaging subject data and exposure conditions supplied from the console 110 are received by the wireless communication unit 60.

The electronic cassette 40 is provided with the power source unit 70, with the mentioned various circuits and devices (the gate line driver 52, the signal processor 54, the image memory 56, the wireless communication unit 60, the microcomputer that functions as the cassette controller 58, the bias voltage generator 71 and the like) actuated with power supplied from the power source unit 70. The power source unit 70 has an inbuilt battery (a rechargeable secondary battery) so as not to affect the portability of the electronic cassette 40, and power is supplied to the various circuits and devices from the charged battery. Note that wiring that connects the power source unit 70 to the various circuits and devices is omitted from illustration in FIG. 9.

As shown in FIG. 9, the console 110 is configured by a server/computer, and is equipped with a display 111 that displays for example an operation menu and captured radiographic images, and an operation panel 112 that is configured including plural keys and is input with various types of information and operation instructions.

Moreover, the console 110 according to the present exemplary embodiment is equipped with: a CPU 113 that controls operation of the overall apparatus; ROM 114 that is pre-stored with for example various programs including a control program; RAM 115 that temporarily stores various data; a hard disk drive (HDD) 116 that stores and holds various data; a display driver 117 that controls the display of various information on the display 111; and an operation input detector 118 that detects an operation state of the operation panel 112. The console 110 is further equipped with a wireless communication unit 119 that employs wireless communication to transmit and receive various data such as exposure conditions, described later, between the console 110 and the radiation generator 120, as well as transmitting and receiving various data such as image data between the console 110 and the electronic cassette 40.

The CPU 113, the ROM 114, the RAM 115, the HDD 116, the display driver 117, the operation input detector 118 and the wireless communication unit 119 are connected together through a system bus BUS. The CPU 113 can accordingly access the ROM 114, the RAM 115 and the HDD 116, and the CPU 113 can also control the display of various data on the display 111 through the display driver 117, and control the transmission and reception through the wireless communication unit 119 of various data to and from the radiation generator 120 and the electronic cassette 40. The CPU 113 can also ascertain the operation state of the operation panel 112 by a user through the operation input detector 118.

The radiation generator 120 is equipped with the radiation source 121, a wireless communication unit 123 that transmits and receives various data such as exposure conditions between the radiation generator 120 and the console 110, and a controller 122 that controls the radiation source 121 based on received exposure conditions.

The controller 122 is also configured including a microcomputer, and stores received exposure conditions. These exposure conditions received from the console 110 include data such as tube voltage, tube current, and exposure duration. The controller 122 causes the radiation X to be irradiated from the radiation source 121 based on the received exposure conditions.

The electronic cassette 40 includes a power adjustment function that, in preparation for imaging a radiographic image, adjusts the detection sensitivity during detection of radiation irradiation start based on the imaging subject data and the exposure conditions notified from the console 110 by adjusting the power supply amount from the battery configuring the power source unit 70. Explanation follows regarding this power adjustment function.

The cassette controller 58 of the electronic cassette 40, in preparation for imaging a radiographic image, is notified with the imaging subject data and the exposure conditions through the wireless communication unit 119 of the console 110. The imaging subject data includes for example data such as the imaging target side and imaging orientation of the imaging subject. The exposure conditions include for example data such as tube voltage, tube current, and exposure duration. The cassette controller 58, based on the imaging subject data and the exposure conditions, derives an irradiation amount of radiation that will be irradiated from the radiation source 121 onto the electronic cassette 40 through the imaging subject within a specific period of time during imaging of a radiographic image.

The cassette controller 58 is equipped with a first reference table 500 such as that illustrated in FIG. 10 inside its own storage unit 58C. The cassette controller 58 derives the irradiation amount of radiation to be irradiated onto the radiation irradiation face (imaging face) of the electronic cassette 40 within the specific period of time by searching the first reference table 500 using as keys the imaging subject data and the exposure conditions acquired from the console 110. A to D in FIG. 10 indicate imaging target sites, a1 to a4, b1 to b4, c1 to c4 and d1 to d4 indicate radiation intensity determined by settable tube currents and tube voltages for each of the imaging target sites. X1 to X8 are estimated values of the approximate irradiation amount of radiation that will be irradiated onto the electronic cassette 40 in the specific period of time corresponding to the imaging target sites A to D and to the radiation intensities a1 to d4. The irradiation amount of radiation that will be irradiated onto the electronic cassette 40 within the specific period of time is smaller for imaging target sites that are sites that do not readily transmit radiation (namely that have a high attenuation coefficient) and for sites of great thickness, whereas the irradiation amount is large for opposite cases. The irradiation amount of radiation that will be irradiated onto the electronic cassette 40 within the specific period of time is also smaller the smaller the value of the tube current and tube voltage set for the radiation generator 120. It is accordingly possible to estimate the irradiation amount of radiation that will be irradiated onto the electronic cassette 40 within the specific period of time based on input data such as the imaging target site and the tube voltage and tube current. The first reference table 500 is accordingly stored in the storage unit 58C with the radiation irradiation amounts X1 to X8 derived by testing or simulation, associated with the imaging subject data and the exposure conditions. Note that the first reference table 500 may include other parameters to those described above (parameters such as for example the imaging subject gender, age, height, weight, body fat index, and thickness of imaging target site). The cassette controller 58 may also compute the intensity of radiation attenuated by passing through the imaging subject based on the imaging subject data and the exposure conditions, and then compute the irradiation amount of radiation that will be irradiated onto the electronic cassette 40 within the specific period of time from the computed radiation intensity. The first reference table 500 becomes redundant in such cases, however processing time is required to compute the radiation irradiation amount.

The cassette controller 58 derives a value of a bias voltage to be applied to the sensor portions 13 based on the derived radiation irradiation amount. The cassette controller 58 is also equipped in its own storage unit 58C with a second reference table 501 such as the example illustrated in FIG. 11. The second reference table 501 includes the irradiation amounts X1 to X8 of radiation that will be irradiated onto the electronic cassette 40 within the specific period of time associated with bias voltage values V1 to V8 that should be applied to the sensor portions 13. The cassette controller 58 derives values of bias voltages that should be applied to the sensor portions 13 by searching the second reference table 501 using as keys the radiation irradiation amounts derived based on the imaging subject data and the exposure conditions.

During imaging of a radiographic image, the value of the bias voltage applied to the sensor portions 13 needs to be made comparatively large to raise the detection sensitivity of the sensor portions 13 in cases in which the irradiation amount of radiation that will be irradiated onto the electronic cassette 40 within the specific period of time is comparatively small. The radiation irradiation start cannot be detected accurately in cases in which the detection sensitivity is insufficient, and transition cannot be made to imaging operation despite radiation being irradiated onto the imaging subject. It is however possible to detect the radiation irradiation start even when the detection sensitivity of the sensor portions 13 is somewhat lowered in cases in which the irradiation amount of radiation that will be irradiated onto the electronic cassette 40 within the specific period of time is comparatively large. The value of the bias voltage applied to the sensor portions 13 in such cases can be made comparatively small.

The second reference table 501 is configured from irradiation amounts associated with bias voltages such that the bias voltage to be applied to the sensor portions 13 is smaller the larger the irradiation amount of radiation that will be irradiated onto the electronic cassette 40 within the specific period of time. Namely, during detection of radiation irradiation start the cassette controller 58 identifies the irradiation amount of radiation that will be irradiated onto the electronic cassette 40 and then controls the bias voltage generator 71 such that the bias voltage applied to the sensor portions 13 is smaller the larger the identified irradiation amount. The power supply amount from the battery configuring the power source unit 70 is thereby reduced. According to such a power adjustment function of the electronic cassette 40, it is possible to achieve a reduction in power consumption in an irradiation standby state of the electronic cassette 40, in comparison to cases in which a relatively high bias voltage is applied in a fixed manner irrespective of the radiation irradiation amount.

Note that it is possible to appropriately increase or decrease the number of bias voltage adjustment steps by re-writing the second reference table 501. Moreover, configuration may be made such that a relationship equation between the irradiation amount of radiation that will be irradiated onto the electronic cassette 40 within the specific period of time and the bias voltage is pre-stored in the storage unit 58C, and a cassette controller 38 computes the bias voltage to be applied to the sensor portions 13 from the relationship equation. The second reference table 501 becomes redundant in such cases.

Explanation next follows regarding operation of the imaging system 104 of the present exemplary embodiment.

Figure 12:
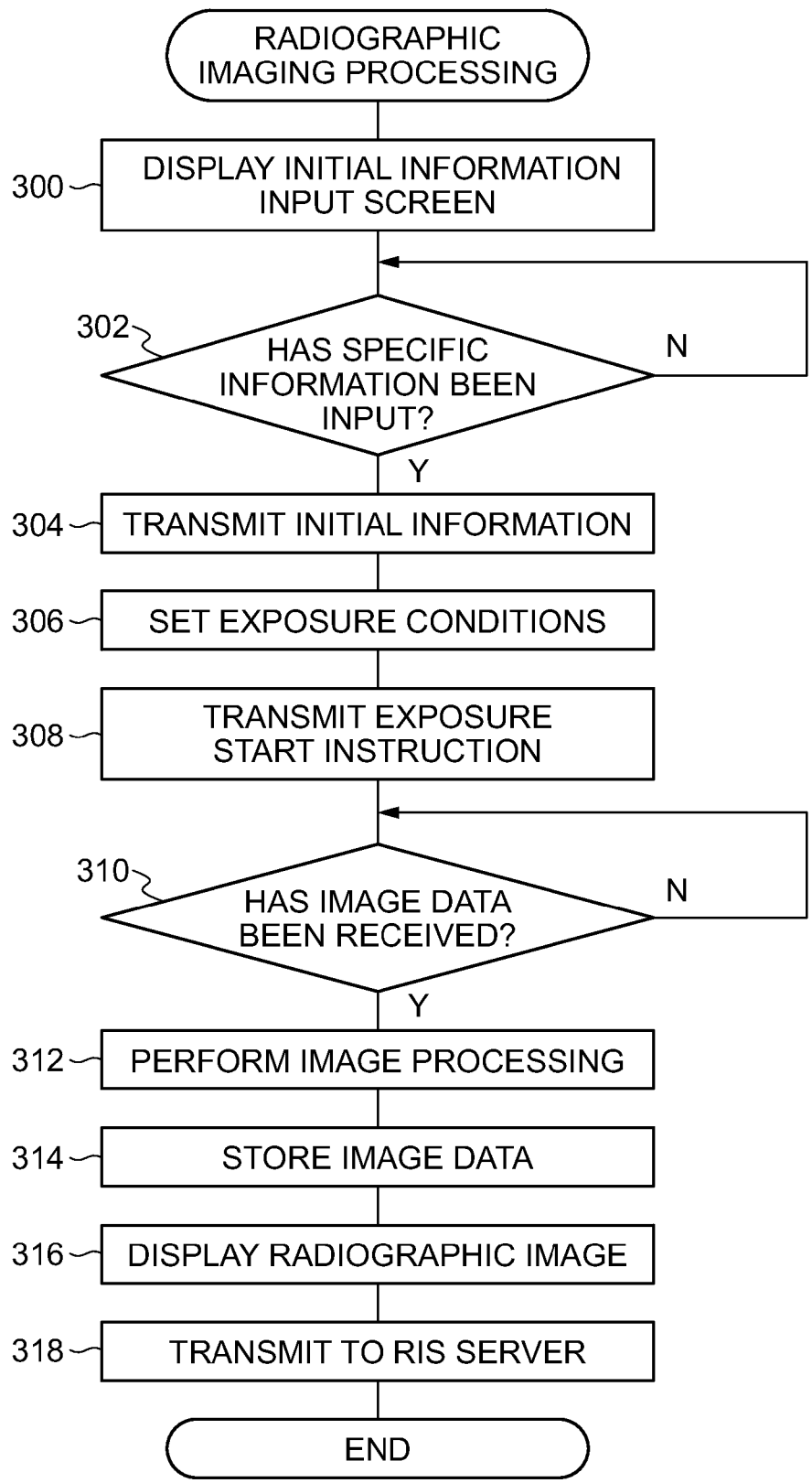
FIG. 12 is a flow chart illustrating a flow of processing in a radiographic imaging processing program according to an exemplary embodiment of the present invention.

First, explanation follows regarding the operation of the console 110 when capturing a radiographic image, with reference to FIG. 12. FIG. 12 is a flow chart showing a flow of processing by a radiographic imaging processing program that is executed by the CPU 113 of the console 110 when input with an instruction to execute radiographic imaging through the operation panel 112. This program is pre-stored in a predetermined region of the ROM 114.

At step 300 in FIG. 12, the CPU 113 controls the display driver 117 so as to cause the display 111 to display a predetermined initial information input screen. At the next step 302, the CPU 113 is on standby for input of specific information.

FIG. 13 shows an example of the initial information input screen that is displayed on the display 111 by the processing of step 300. As shown in FIG. 13, in the initial information input screen according to the present exemplary embodiment, a message is displayed prompting input of the name of the patient (imaging subject) on whom radiographic imaging is to be performed, the imaging target site, the posture during imaging, and the exposure conditions of the radiation X during imaging (in the present exemplary embodiment, the tube voltage, the tube current and exposure duration during radiation X exposure). Input fields for these items of information are also displayed.

After the initial information input screen shown in FIG. 13 is displayed on the display 111, the radiographer inputs the name of the patient (imaging subject) to be imaged, the imaging target site, the posture during imaging, and the exposure conditions into the corresponding input fields through the operation panel 112.

The radiographer enters the radiographic imaging room 180 with the patient (imaging subject). When performing image capture in a standing position or prone position, the radiographer positions the patient (imaging subject) at a specific imaging position (performs positioning) after the electronic cassette 40 has been held by holder 162 of the upright stand 160 or the holder 166 of the prone table 164 as appropriate and the radiation source 121 has been positioned correspondingly. However in order to perform radiographic imaging with the electronic cassette 40 not held by a holder, such as when the imaging target site is a region of an arm or leg, the radiographer positions the patient (imaging subject) in a specific imaging position (performs positioning). However, when capturing a radiographic image of an imaging target site such as an arm or a leg without the electronic cassette 40 being held in the holders, the radiographer positions (performs positioning of) the patient (imaging subject), the electronic cassette 40 and the radiation source 121 in a state that allows imaging of the imaging target site.

The radiographer then exits the radiographic imaging room 180, and uses the operation panel 112 to select the INPUT COMPLETE button displayed in the vicinity of the bottom edge of the initial information input screen. Step 302 is determined in the affirmative when the radiographer has selected the INPUT COMPLETE button and processing then transitions to step 304.

At step 304 the CPU 113 transmits the data input to the initial information input screen (referred to below as "initial information") to the electronic cassette 40 through the wireless communication unit 119. Then at the next step 306 the exposure conditions are set by transmitting the exposure conditions included in the initial information to the radiation generator 120 through the wireless communication unit 119. The controller 122 of the radiation generator 120 then performs preparation for exposure according to the received exposure conditions.

At the next step 308, the CPU 113 transmits instruction data instructing the start of exposure to the radiation generator 120 and the electronic cassette 40 through the wireless communication unit 119.

In response the radiation source 121 starts emitting the radiation X with the tube voltage and tube current corresponding to the exposure conditions the radiation generator 120 has received from the console 110. The radiation X emitted from the radiation source 121 reaches the electronic cassette 40 after passing through the patient (imaging subject).

The cassette controller 58 of the electronic cassette 40 receives the instruction data instructing the start of exposure, and remains on standby until the radiation amount detected by the radiation detection pixels 32A reaches a predetermined threshold value or greater that serves as a value for detecting that radiation irradiation has started. The electronic cassette 40 starts radiographic imaging operation when determination is made that the radiation amount detected by the radiation detection pixels 32A has reached the threshold value or greater. The electronic cassette 40 ends the radiographic imaging operation after a specific accumulation duration has elapsed since the start of radiation irradiation, and then transmits the thus obtained image data to the console 110.

At the next step 310, the CPU 113 enters standby until the image data is received from the electronic cassette 40, and at the next step 312, image processing is performed on the received image data to perform various corrections such as shading correction after the missing pixel correction processing described above has been performed.

Then at the next step 314 the CPU 113 stores in the HDD 116 the image data that has been subject to image processing (referred to below as "corrected image data"). Then at the next step 316 the display driver 117 is controlled so as to display a radiographic image expressed by the corrected image data on the display 111, in order for example to perform verification.

At the next step 318 the CPU 113 transmits the corrected image data to the RIS server 150 over the in-hospital network 102, after which the radiographic imaging processing program is ended. The corrected image data transmitted to the RIS server 150 is stored in the database 150A, thereby enabling a medical doctor to read the captured radiographic image and perform diagnostics.

Figure 14:
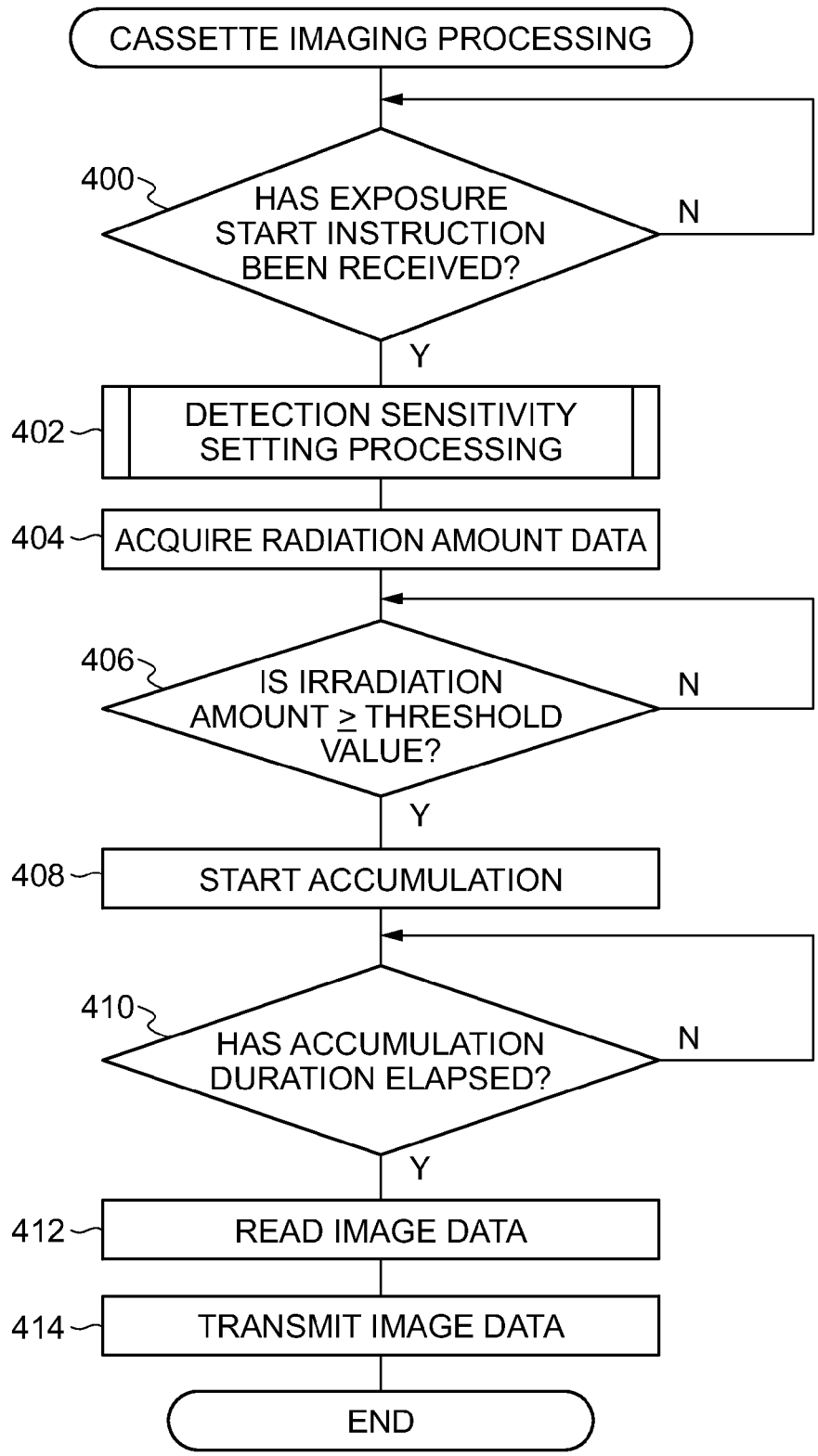
FIG. 14 is a flow chart illustrating a processing flow in a cassette imaging processing program according to an exemplary embodiment of the present invention.

Explanation follows regarding operation of the electronic cassette 40 when the initial information is received from the console 110, with reference to FIG. 14. FIG. 14 is a flow chart illustrating the flow of processing of a cassette imaging processing program executed by the CPU 58A of the cassette controller 58 in the electronic cassette 40 when initial information is received from the console 110. The cassette imaging program is pre-stored in a specific region of the storage unit 58C of the cassette controller 58.

At step 400, the CPU 58A awaits receipt of instruction data instructing exposure start, described above, from the console 110. At the next step 402 the following detection sensitivity setting processing program is executed.

Figure 15:
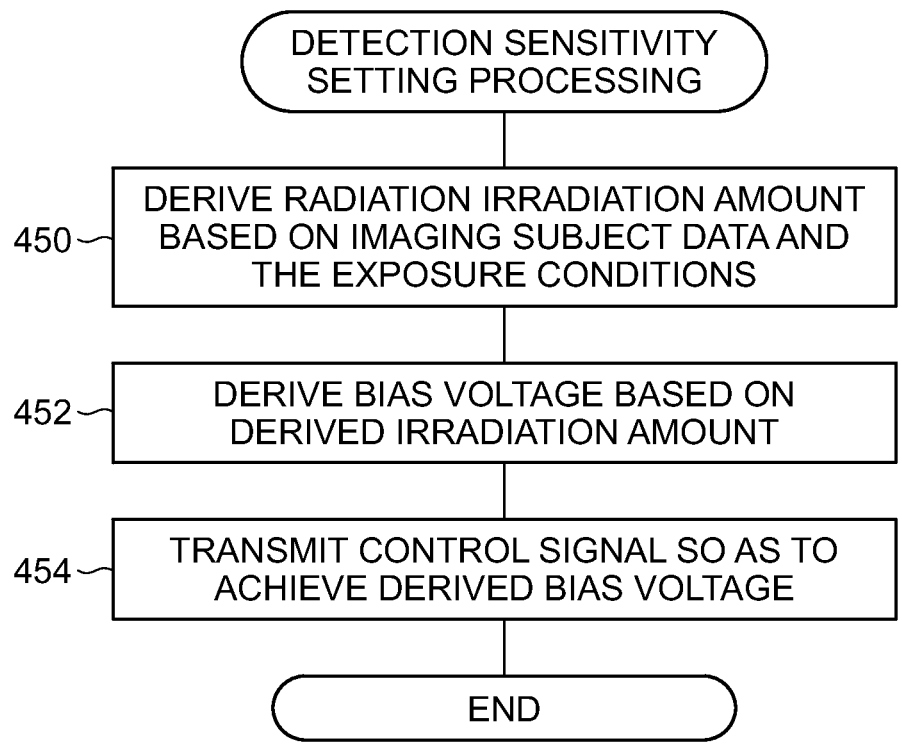
FIG. 15 is a flow chart illustrating a flow of processing in a radiographic imaging processing program according to an exemplary embodiment of the present invention.

FIG. 15 is a flow chart indicating a flow of processing of the detection sensitivity setting processing program executed in the CPU 58A. This program is also pre-stored in a specific region of the storage unit 58C of the cassette controller 58.

At step 450 of FIG. 15, the CPU 58A derives the irradiation amount of radiation that will be irradiated onto the electronic cassette 40 within the specific period of time by searching the first reference table 500 (see FIG. 10) stored in the storage unit 58C using as keys the imaging target site as the imaging subject data, and the tube current and the tube voltage as the exposure conditions, that are contained in initial information supplied from the console 110.

In the next step 452, the CPU 58A derives a value of the bias voltage that should be applied to the sensor portions 13 by searching the second reference table 501 (see FIG. 11) stored in the storage unit 58C using as a key the radiation irradiation amount derived at step 450. Note that the second reference table 501 is configured to derive a smaller value bias voltage the larger the radiation irradiation amount derived at step 450.

In the next step 454, the CPU 58A supplies to the bias voltage generator 71 the control signal required to apply the bias voltage derived at step 452 to the sensor portions 13, so as to control the output voltage of the bias voltage generator 71. The present detection sensitivity setting processing program is then ended. On receipt of the control signal, the bias voltage generator 71 outputs the bias voltage derived by the CPU 58A, and applies this bias voltage to each of the sensor portions 13.

Transition is made to step 404 of a cassette imaging processing program (main routine) when the detection sensitivity setting processing program has ended. At step 404, the CPU 58A supplies a control signal to the signal processor 54 and processing to read charge from the radiation detection pixels 32A is executed in the signal processor 54. The amount of charge read from the radiation detection pixels 32A is temporarily stored in the memory 58B of the cassette controller 58 as radiation amount data (a detection signal) indicating the dose of radiation that has been irradiated. The CPU 58A acquires the radiation amount data (a detection signal) by accessing the memory 58B.

In the next step 406, the CPU 58A determines whether or not a radiation dose indicated in the radiation amount data (a detection signal) previously acquired at step 404 is a predetermined specific threshold value for detecting radiation irradiation start or greater. Processing returns to step 404 when determination is negative at step 406. However, affirmative determination is taken to mean that emission of radiation from the radiation source 121 has started, and processing transitions to step 408. Note that configuration may be made such that at this point in time the CPU 58A supplies the gate line driver 52 with a control signal required to perform a reset operation for discharging dark current that has accumulated in the radiation detection pixels 32A and the radiographic imaging pixels 32B up until radiation irradiation start has been detected. On receipt of such a control signal, the gate line driver 52 then supplies a drive signal sequentially to the gate lines 34 so as to switch the thin film transistors 100N one line at a time. Any dark current that has accumulated in the radiation detection pixels 32A and the radiographic imaging pixels 32B is thereby discharged to the signal lines 36, resetting each of the pixels.

In the next step 408, the CPU 58A supplies the gate line driver 52 with a control signal required to switch all the thin film transistors 10 OFF. Accordingly, accumulation starts of charge generated in the radiographic imaging pixels 32B according to the irradiation of radiation, and transition is made to the imaging operation of a radiographic image. When this is performed, the CPU 58A may be configured to set the bias voltage to be applied to the sensor portions 13 of the radiographic imaging pixels 32B to a different voltage to the bias voltage derived in step 452 (see FIG. 15). For example, the CPU 58A may at the present step 408 supply the bias voltage generator 71 with a control signal required to set an upper limit value to a bias voltage setting range. Namely, the detection sensitivity of the sensor portions 13 during imaging of a radiographic image may be set higher than the detection sensitivity during radiation irradiation start detection. The CPU 58A thereby controls the detection sensitivity to radiation during imaging of a radiographic image independently from the detection sensitivity during radiation irradiation start detection.

In the next step 410, the CPU 58A determines whether or not a specific accumulation duration has elapsed since transition to the accumulation operation. The accumulation duration is set according to the exposure duration of radiation set as the exposure conditions. The CPU 58A transitions to the processing of step 412 when determined that the specific accumulation duration has elapsed since transition to the accumulation operation.

At the next step 412, the CPU 58A causes an ON signal to be output from the gate line driver 52 to the gate lines 34 in sequence one line at a time by supplying a control signal to the gate line driver 52. Each of the thin film transistors 10 connected to each of the gate lines 34 is thereby switched ON in sequence one line at a time. The charge that has been accumulated in each of the capacitors 9 is thereby read into each of the signal lines 36, and converted by the signal processor 54 into digital image data which is then stored in the image memory 56.

At the next step 414, the CPU 58A reads the image data stored in the image memory 56 and the present cassette imaging processing program is ended after transmitting the read image data to the console 110 through the wireless communication unit 60.

In the electronic cassette 40 of the present exemplary embodiment, as shown in FIG. 8, the radiation detector 20 is disposed such that radiation X is irradiated from the TFT substrate 30 side of the electronic cassette 40.

Figure 16:
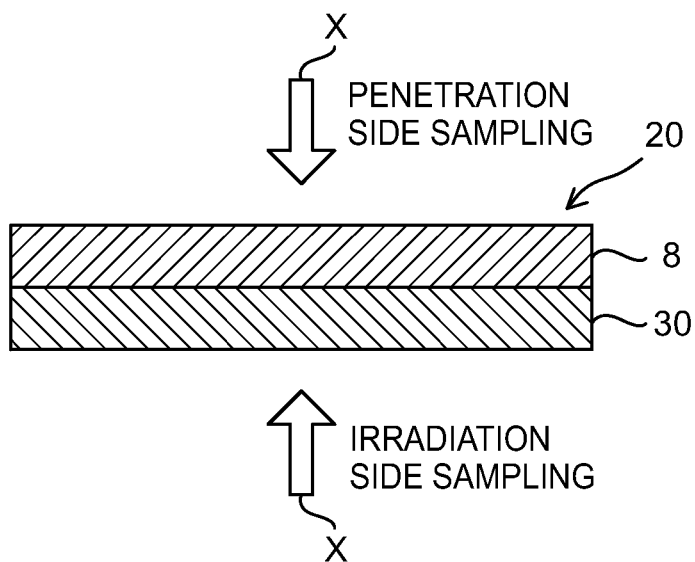
FIG. 16 is a side on cross-section to explain an irradiation side sampling method and a penetration side sampling method of radiographic imaging.
Figure 18:
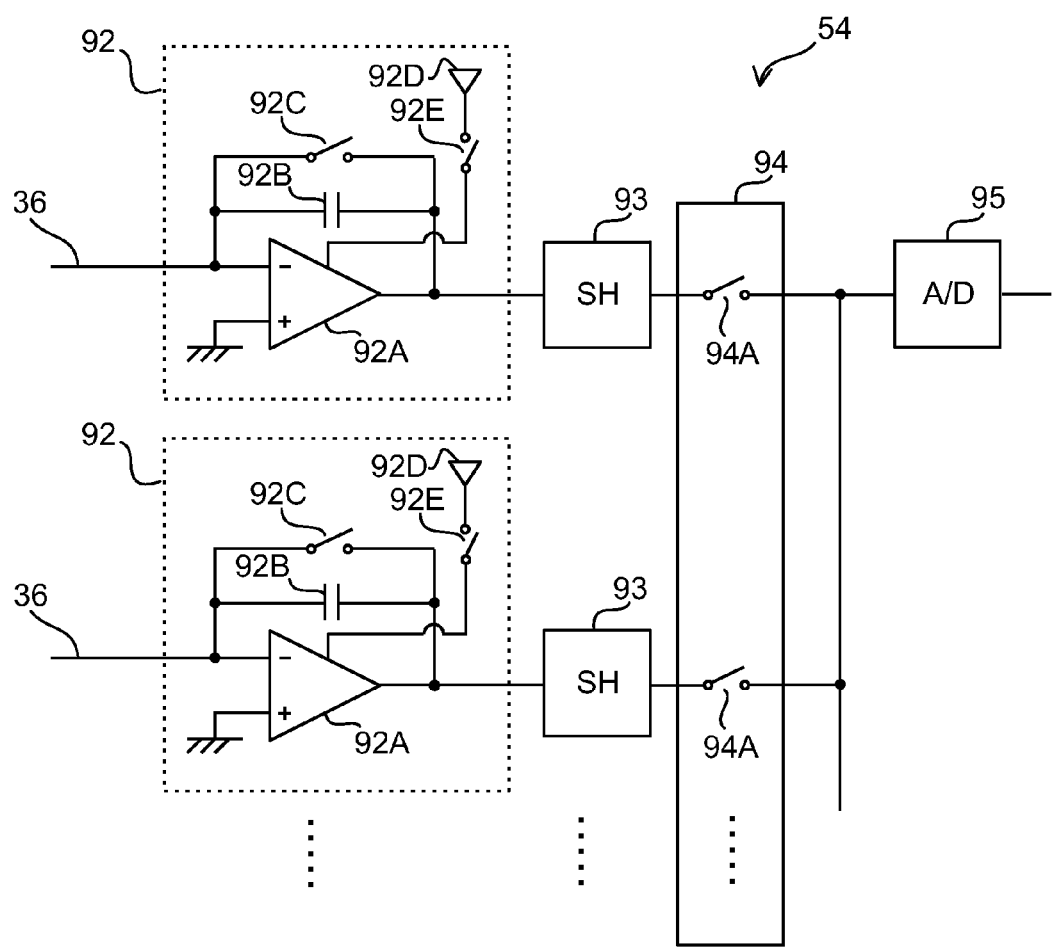
FIG. 18 is a diagram illustrating a configuration of a signal processor according to an exemplary embodiment of the present invention.

In cases using what is referred to as a Penetration Side Sampling (PSS) method in which the radiation detector 20 is irradiated with radiation from the side on which the scintillator 8 is formed, as shown in FIG. 16, and radiographic images are read by the TFT substrate 30 provided on the opposite side to the radiation incident face, light is emitted with higher intensity from the top face side of the scintillator 8 in FIG. 18 (the opposite side to the face joined to the TFT substrate 30). However, in cases using what is referred to as an Irradiation Side Sampling (ISS) method in which radiation is irradiated from the TFT substrate 30 side and radiographic images are read by the TFT substrate 30 provided on the radiation incident face side, radiation that has passed through the TFT substrate 30 is incident to the scintillator 8 and light is emitted with higher intensity from the side of the scintillator 8 of the face joined to the TFT substrate 30. Each of the sensor portions 13 provided to the TFT substrate 30 generates charge according to the light generated in the scintillator 8. The radiographic images captured are accordingly of higher resolution when an ISS method is employed than when a PSS method is employed since the light emission position of the scintillator 8 is closer to the TFT substrate 30.

The radiation detector 20 is also configured with the photoelectric conversion layer 4 formed from an organic photoelectric conversion material and so radiation is barely absorbed by the photoelectric conversion layer 4. The radiation detector 20 of the present exemplary embodiment is accordingly capable of suppressing deterioration in sensitivity to radiation, since the amount of radiation absorbed by the photoelectric conversion layer 4 is smaller even when radiation passes through the TFT substrate 30 due to employing an ISS method. In an ISS method the radiation has passed through the TFT substrate 30 to reach the scintillator 8. However application may be made to an ISS method when the photoelectric conversion layer 4 of the TFT substrate 30 is thus configured from an organic photoelectric conversion material, since there is hardly any radiation absorption in the photoelectric conversion layer 4 and radiation attenuation can be suppressed to a small amount.

It is also possible to form both the amorphous oxide configuring the active layer 17 of the thin film transistors 10 and the organic photoelectric conversion material configuring the photoelectric conversion layer 4 using film forming at low temperature. The substrate 1 can accordingly be formed from plastic resin with aramid and/or bionanofibers, having low absorptivity to radiation. Since the amount of radiation absorbed by the thus formed substrate 1 is small, sensitivity to radiation can be suppressed from deteriorating even when radiation passes through the TFT substrate 30 due to employing an ISS method.

According to the present exemplary embodiment, as shown in FIG. 8, the radiation detector 20 is attached inside the housing 41 to the top plate 41B so that the TFT substrate 30 is on the top plate 41B side. Moreover, the top plate 41B of the housing 41 can be formed thinner in cases in which the substrate 1 is formed with high rigidity from a plastic resin with aramid and/or bionanofibers, since the rigidity of the radiation detector 20 itself is high. The radiation detector 20 is also not easily damaged in cases in which the substrate 1 is formed with high rigidity from a plastic resin with aramid and/or bionanofibers, even when the imaging region 41A incurs an impact since the radiation detector 20 itself is flexible.

As explained in the above, based on the imaging subject data and the exposure conditions supplied from the console 110, the electronic cassette 40 according to an exemplary embodiment of the present invention derives an irradiation amount of radiation that will be irradiated onto the electronic cassette 40 within the specific period of time prior to radiation actually being irradiated from the radiation source 121. The electronic cassette 40 then derives a value for the bias voltage that should be applied to the sensor portions 13 based on the derived radiation irradiation amount, thereby setting the detection sensitivity to radiation irradiation start. When doing so, the electronic cassette 40 makes the power supply amount from the power source unit 70 smaller the larger the derived radiation irradiation amount, thereby lowering the detection sensitivity to radiation irradiation start. Namely, the cassette controller 58 controls such that the value of the bias voltage is smaller the larger the derived radiation irradiation amount. The electronic cassette 40 thus changes the bias voltage to be applied to the sensor portions 13 to appropriately adjust the detection sensitivity according to the anticipated radiation irradiation amount. It is accordingly possible to prevent application of a bias voltage excessively larger than the bias voltage needed to detect the radiation irradiation start. A reduction in power consumption in the irradiation standby state is accordingly possible in comparison to cases in which an excessive bias voltage is applied in a fixed manner irrespective of the radiation irradiation amount. The electronic cassette 40 appropriately adjusts the detection sensitivity to radiation according to the anticipated radiation irradiation amount, and so false detection of radiation irradiation start can be prevented in comparison to cases in which a constant high sensitivity is set.

Figure 17:
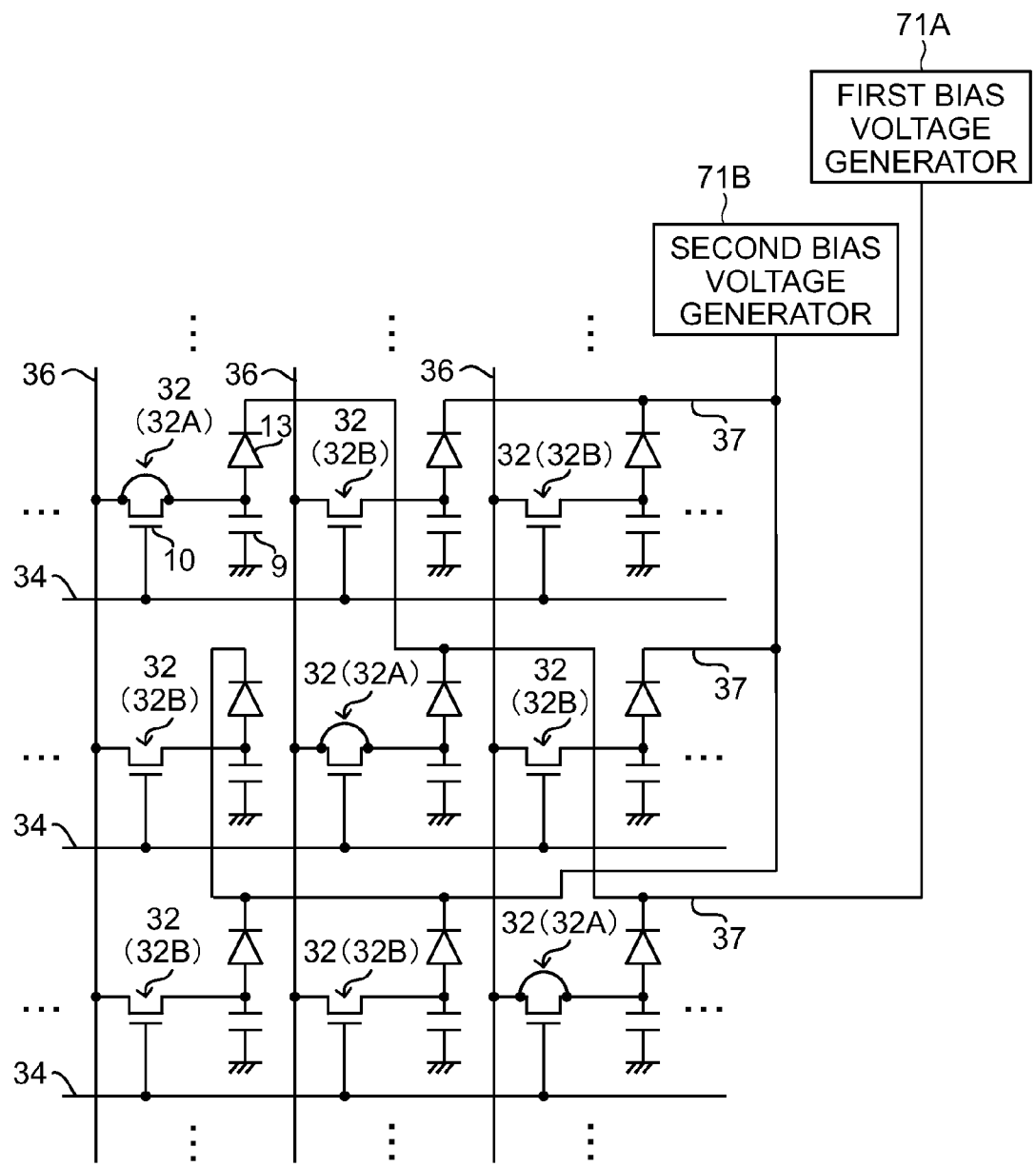
FIG. 17 is a diagram illustrating another configuration of an electronic cassette according to an exemplary embodiment of the present invention.

Note that in the present exemplary embodiment, an example has been illustrated in which the sensor portions 13 of the radiation detection pixels 32A and the sensor portions 13 of the radiographic imaging pixels 32B are connected to the common bias voltage generator 71 through the bias lines 37, however there is no limitation thereto. Namely, as illustrated in FIG. 17, a first bias voltage generator 71A for supplying a bias voltage to the sensor portions 13 of the radiation detection pixels 32A and a second bias voltage generator 71B for supplying a bias voltage to the sensor portions 13 of the radiographic imaging pixels 32B may be separately provided. In such cases, during detection of radiation irradiation start, the output voltage of the first bias voltage generator 71A that applies bias voltage to the sensor portions 13 of the radiation detection pixels 32A is controlled according to the anticipated radiation irradiation amount similarly to in the exemplary embodiment described above. Moreover, in such cases control may be performed to stop the supply of bias voltage from the first bias voltage generator 71A after radiation irradiation start has been detected by the radiation detection pixels 32A. It is thereby possible to achieve an even greater reduction in power consumption. However, the output voltage of the second bias voltage generator 71B for applying bias voltage to the sensor portions 13 of the radiographic imaging pixels 32B is controlled independently from the first bias voltage generator 71A so as to be a voltage appropriate to imaging a radiographic image.

Second Exemplary Embodiment

Explanation follows regarding an electronic cassette according to a second exemplary embodiment of the present invention. The electronic cassette 40 according to the first exemplary embodiment derives an irradiation amount of radiation that will be irradiated onto the electronic cassette 40 within the specific period of time, and adjusts the power supply amount from the power source unit 70 by adjusting the value of the bias voltage applied to the sensor portions 13 according to the derived radiation irradiation amount. In the electronic cassette 40 according to the second exemplary embodiment, however, the power supply amount from a power source unit 70 is adjusted by adjusting the number of drive times of a charge amplifier configuring a signal processor 54 according to the derived radiation irradiation amount.

FIG. 18 is a diagram illustrating a configuration of the signal processor 54 configuring the electronic cassette 40. Note that since configuration portions other than the signal processor 54 are similar to those of the first exemplary embodiment, explanation thereof is omitted.

As illustrated in FIG. 18, the signal processor 54 includes charge amplifiers 92 respectively connected to each of the signal lines 36. Note that one or more radiation detection pixels 32A is connected to each of the signal lines 36. Each of the charge amplifiers 92 includes: an operational amplifier (operation amplification circuit) 92A with inverting input terminal connected to the respective signal line 36 and non-inverting input terminal connected to a ground potential; a capacitor 92B with one terminal connected to the inverting input terminal of the operational amplifier 92A and the other terminal connected to the output terminal of the operational amplifier 92A; and a reset switch 92C that is connected in parallel to the capacitor 92B. Each of the charge amplifiers 92 also includes a switch 92E between a power line 92D and a power input terminal of the operational amplifier 92A. Namely, the operational amplifiers 92 are each placed in an operational state supplied with drive voltage from the power line 92D by switching the switch 92E ON. ON/OFF switching of the switches 92E is performed according to a control signal supplied from the cassette controller 58.

The charges generated in each of the radiation detection pixels 32A during radiation irradiation start detection are accumulated in the capacitors 92B of the charge amplifiers 92 through the signal lines 36. The charge amplifiers 92 generate electric signals with a signal level corresponding to the charge amount accumulated in the capacitors 92B. These electric signals are supplied to sample-and-hold circuits 93. The electric signals output from the charge amplifiers 92 are reset every fixed cycle by the reset switches 92C being placed in an ON state in response to a control signal supplied from the cassette controller 58. The output terminal of each of the charge amplifiers 92 is connected to the input terminal of the sample-and-hold circuits 93.

The sample-and-hold circuits 93 hold the signal level of the electric signals supplied from the charge amplifiers 92 in response to a control signal supplied from the cassette controller 58. Namely, the sample-and-hold circuits 93 perform sampling of the signal levels of the electric signals output from the charge amplifiers 92 at a specific sampling cycle. The output terminals of each of the sample-and-hold circuits 93 are connected to a common multiplexer 94.

The multiplexer 94 sequentially selects and outputs the signal levels held in the sample-and-hold circuits 93 according to a control signal supplied from the cassette controller 58. Namely, the multiplexer 94 converts electrical signals from the sample-and-hold circuits 93 into serial data and supplies the serial data to an A/D (analogue-digital) converter 95.

The A/D converter 95 converts the signal levels of the electrical signals sequentially supplied from the multiplexer 94 into digital signals, and temporarily stores digital values obtained thereby as radiation amount data (detection signals) in the memory 58B of the cassette controller 58.

During radiation irradiation standby the cassette controller 58 executes processing in the signal processor 54 to read charges accumulated in the radiation detection pixels 32A, and accesses the memory 58B to acquire radiation amount data (a detection signal) that indicates the amount of charge read from the radiation detection pixels 32A, namely the dose of radiation irradiated. The cassette controller 58 for example sums the radiation amount data (a detection signal) for each of the signal lines 36 sequentially output from the A/D converter 95, and determines that emission of radiation from the radiation source 121 has started when determined that the summed value thereby obtained is a predetermined specific threshold value for detecting radiation irradiation start or greater.

The electronic cassette 40 according to the present exemplary embodiment also, in preparation for imaging a radiographic image, has a power adjustment function that adjusts the power supply amount from the battery configuring the power source unit 70 by adjusting the detection sensitivity during radiation irradiation start detection based on the imaging subject data and the exposure conditions notified from the console 110. The power adjustment function according to the present exemplary embodiment is explained below.

The cassette controller 58, similarly to in the first exemplary embodiment, is equipped with a first reference table 500 such as that illustrated in FIG. 10 inside its own storage unit 58C. The cassette controller 58 derives the irradiation amount of radiation that will be irradiated onto the electronic cassette 40 within the specific period of time by searching the first reference table 500 using as keys the imaging subject data and the exposure conditions acquired from the console 110. A to D in FIG. 10 indicate imaging target sites, a1 to a4, b1 to b4, c1 to c4 and d1 to d4 indicate radiation intensity determined by settable tube currents and tube voltages for each of the imaging target sites. Note that the cassette controller 58 may also compute the intensity of radiation attenuated by passing through the imaging subject based on the imaging subject data and the exposure conditions, and then compute the irradiation amount of radiation that will be irradiated onto the electronic cassette 40 within the specific period of time from the computed radiation intensity. The first reference table 500 becomes redundant in such cases, however processing time is required to compute the radiation irradiation amount.

The cassette controller 58 derives the number of times for driving the charge amplifiers 92 of the signal processor 54 based on the derived radiation irradiation amount. The cassette controller 58 is equipped with a third reference table 502 such as that illustrated in FIG. 19 stored in its own storage unit 58C. The third reference table 502 includes the irradiation amounts X1 to X8 of radiation that will be irradiated onto the electronic cassette 40 within the specific period of time associated with numbers N1 to N8 of the charge amplifiers 92 that should be driven. The cassette controller 58 derives the number of the charge amplifiers 92 that should be driven (drive number) by searching the third reference table 502 using as keys the derived radiation irradiation amounts.

As explained above, the cassette controller 58 sums the digital values corresponding to each of the signal lines 36 sequentially output from the A/D converter 95, and detects radiation irradiation start based on the summed value thereby obtained. During imaging of a radiographic image, in cases in which the irradiation amount of radiation that will be irradiated onto the electronic cassette 40 within the specific period of time is relatively small, the detection sensitivity to radiation irradiation start needs to be raised by making the charge amplifier 92 drive number relatively large, thereby increasing the summed value obtained above. However, when the irradiation amount of radiation that will be irradiated onto the electronic cassette 40 within the specific period of time is relatively large, a sufficiently large summed value can be obtained even with a reduced charge amplifier 92 drive number and lower detection sensitivity to radiation irradiation start. In the electronic cassette 40 according to the present exemplary embodiment the detection sensitivity to radiation irradiation start is adjusted by controlling the charge amplifier 92 drive number.

In the third reference table 502 irradiation amounts and charge amplifier 92 drive numbers are associated with each other such that the charge amplifier 92 drive number gets smaller the larger the irradiation amount of radiation that will be irradiated onto the electronic cassette 40 within the specific period of time. Namely, during radiation irradiation start detection, the cassette controller 58 identifies the irradiation amount of radiation that will be irradiated onto the electronic cassette 40 within the specific period of time, and controls the switches 92E of the signal processor 54 such that the charge amplifier drive number is smaller the larger the identified irradiation amount. It is accordingly possible to achieve a reduction in power consumption in the irradiation standby state compared to cases in which all the charge amplifiers 92 are always driven and a high detection sensitivity is always maintained irrespective of the radiation irradiation amount.

Note that it is possible to appropriately increase or decrease the number of drive number adjustment steps by re-writing the third reference table 502. Moreover, configuration may be made such that a relationship equation between the irradiation amount of radiation that will be irradiated onto the electronic cassette 40 within the specific period of time and the charge amplifier 92 drive number is pre-stored in the storage unit 58C, and a cassette controller 38 computes the charge amplifier 92 drive number from the relationship equation.

Moreover, configuration may be made such that instead of the charge amplifier 92 drive number, or as well as the drive number, the cassette controller 58 derives which of the charge amplifiers 92 connected to which of the signal lines 36 to drive. In such cases, determination is made as to which of the radiation detection pixels 32A disposed at which position on the TFT substrate 30 to make active. The charge amplifiers 92 to be driven are preferably derived by the cassette controller 58 such that the active radiation detection pixels 32A are not unevenly distributed on the TFT substrate 30. In other words, preferably the charge amplifiers 92 to be driven are derived such that the active radiation detection pixels 32A are uniformly distributed on the TFT substrate 30. For example, the cassette controller 58 may be set to control such that the charge amplifiers 92 to be driven are disposed on every other line, or on one line every plural number of lines.

Figures 19, 20:
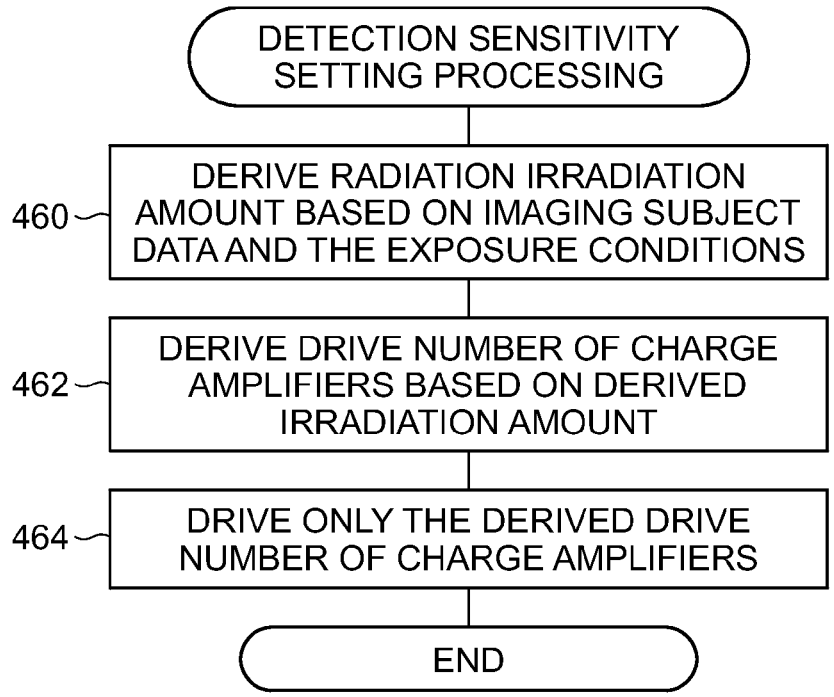
FIG. 19 is diagram illustrating a third reference table according to an exemplary embodiment of the present invention.
FIG. 20 is a flow chart illustrating a flow of processing in a detection sensitivity setting processing program according to another exemplary embodiment of the present invention.

Explanation follows regarding a detection sensitivity setting processing program according to the present exemplary embodiment executed at step 402 of the cassette imaging processing program illustrated in FIG. 14, with reference to FIG. 20. FIG. 20 is a flow chart illustrating a flow of processing of the detection sensitivity setting processing program according to the present exemplary embodiment executed by the CPU 58A of the cassette controller 58, and corresponds to the flow chart according to the detection sensitivity setting processing program according to the first exemplary embodiment illustrated in FIG. 15.

At step 460 of FIG. 20, the CPU 58A derives the irradiation amount of radiation that will be irradiated onto the electronic cassette 40 within the specific period of time by searching the first reference table 500 (see FIG. 10) stored in the storage unit 58C using as keys the imaging target site as the imaging subject data and the tube current and tube voltage as the exposure conditions contained in the initial information supplied from the console 110.

In the next step 462, the CPU 58A derives the charge amplifier 92 drive number corresponding to this irradiation amount by searching the third reference table 502 (see FIG. 19) stored in the storage unit 58C using as a key the radiation irradiation amount derived at step 460. Note that the third reference table 502 is configured such that drive numbers with smaller values are derived the larger the radiation irradiation amount derived at step 460.

At the next step 464, the CPU 58A selectively switches the switches 92E provided between the power input terminal of the charge amplifiers 92 and the power line to the ON state to achieve the drive number derived at step 462. The present detection sensitivity setting processing program is then ended. In the signal processor 54, only the switches 92E of the charge amplifiers 92 selected by the cassette controller 58 are placed in the ON state, and power is only supplied to the drive number of the charge amplifiers 92 derived at step 462.

Note that transition is made to the radiographic image imaging operation after radiation irradiation start has been detected and charges generated according to irradiated radiation start to accumulate in the radiographic imaging pixels 32B. When this is performed, the CPU 58A may be configured to set the charge amplifier 92 drive number to a different drive number to that derived in step 462. For example, the CPU 58A may control the switches 92E required to drive all the charge amplifiers 92. Namely, the radiation detection sensitivity during imaging a radiographic image may be set higher than the radiation detection sensitivity during radiation irradiation start detection. The CPU 58A thereby controls the detection sensitivity to radiation during imaging the radiographic image independently to the radiation detection sensitivity during radiation irradiation start detection.

As explained above, the electronic cassette 40 according to an exemplary embodiment of the present invention derives the irradiation amount of radiation that will be irradiated onto the electronic cassette 40 within the specific period of time prior to radiation actually being irradiated from the radiation source 121 based on the imaging subject data and exposure conditions supplied from the console 110. The electronic cassette 40 then derives a value for the charge amplifier 92 drive number based on the derived radiation irradiation amount, thereby setting the detection sensitivity to radiation irradiation start. When doing so, the electronic cassette 40 makes the power supply amount from the power source unit 70 smaller the larger the derived radiation irradiation amount, thereby lowering the detection sensitivity to radiation irradiation start. Namely, the electronic cassette 40 is controlled such that the charge amplifier 92 drive number is smaller the larger the derived radiation irradiation amount. The cassette controller 58 accordingly changes the charge amplifier 92 drive number to appropriately adjust the detection sensitivity according to the anticipated radiation irradiation amount. It is accordingly possible to prevent use of more of the charge amplifiers 92 than are needed to detect the radiation irradiation start. A reduction in power consumption in the irradiation standby state is accordingly possible in comparison to cases in which all the charge amplifiers 92 are driven irrespective of the radiation irradiation amount. The electronic cassette 40 appropriately adjusts the detection sensitivity to radiation according to the anticipated radiation irradiation amount, and so false detection of radiation irradiation start can be prevented in comparison to cases in which a constant high sensitivity is set.

Thus in the present exemplary embodiment, the number of radiation detection pixels 32A that are active (active number) is adjusted by the charge amplifier 92 drive number based on the derived radiation irradiation amount to adjust the power supply amount from the power source unit 70. Another example of a method for adjusting the number of radiation detection pixels 32A that are active (active number) is a method of adjusting the number of sensor portions 13 to which the bias voltage is applied. Consequently, the cassette controller 58 may be configured to adjust the individual number of the sensor portions 13 to which the bias voltage is applied according to the derived radiation irradiation amount, either in place of adjusting the charge amplifier 92 drive number, or as well as adjusting the charge amplifier 92 drive number.

The cassette controller 58 of the electronic cassette 40 may execute the following control to control the signal processor 54 to lower the detection sensitivity to radiation irradiation start by making the power supply amount to the signal processor 54 smaller the larger the derived radiation irradiation amount.

Namely, the cassette controller 58 derives a first value as a setting value for gain of the charge amplifiers 92 in cases in which the irradiation amount of radiation that will be irradiated within the specific period of time derived based on the imaging subject data and the exposure conditions is smaller than a specific threshold value. However, the cassette controller 58 derives a second value smaller than the first value as the setting value for gain of the charge amplifiers 92 in cases in which the derived radiation irradiation amount is greater than the specific threshold value. Consequently, the electronic cassette 40 controls the gain of the charge amplifiers 92 according to the derived radiation irradiation amount, and so setting gain excessively larger than the appropriate gain needed for radiation irradiation start detection can be prevented. It is accordingly possible to achieve a reduction in power consumption in the irradiation standby state compared to cases in which a comparatively high gain is set in a fixed manner irrespective of the radiation irradiation amount. Note that to make the gain of the charge amplifiers 92 variable, configuration may be made such that plural capacitors with different capacitance values to each other are selectively connected between the input terminals and the output terminals of the operational amplifiers 92A. Moreover, in the above explanation an example is given of a case in which gain is adjusted to two levels employing a single threshold value, however a configuration is possible in which the gain can be varied to three or more levels employing two or more threshold values.

Moreover, the cassette controller 58 of the electronic cassette 40 may execute the following control. Namely, the cassette controller 58 executes correction processing to remove noise components from the radiation amount data (a detection signal) generated in the signal processor 54 in cases in which the radiation irradiation amount derived based on the imaging subject data and the exposure conditions is smaller than a specific threshold value. In such cases, noise data that is employed in the correction processing is acquired. The noise data is, for example, acquired by storing radiation amount data (a detection signal) in a radiation non-irradiation state in the memory 58B. Although executing such correction processing raises the detection sensitivity to radiation irradiation start, attempting to store noise data in the memory 58B and retain this noise data consumes power. However, the cassette controller 58 omits the above described correction processing in cases in which the radiation irradiation amount derived based on the imaging subject data and the exposure conditions is larger than the specific threshold value. Although detection sensitivity to radiation irradiation start is thereby lowered compared to cases in which the correction processing is executed, since the processing to acquire noise data and the processing to hold the noise data in the memory 58B is not required, it is possible to achieve a saving in the power consumption of the amount that would have been needed for such processing. Due to omitting execution of the correction processing according to the anticipated radiation irradiation amount, the electronic cassette 40 is accordingly able to achieve a reduction in power consumption in the irradiation standby state compared to cases in which the correction processing is always executed irrespective of the radiation irradiation amount. Note that in the above exemplary embodiment an example is given of a case in which the correction processing is omitted according to the radiation irradiation amount, however there is no limitation thereto and other processing that contributes to raising the detection sensitivity during radiation irradiation start detection may be employed.

Third Exemplary Embodiment

Explanation follows regarding an electronic cassette according to a third exemplary embodiment of the present invention. In the electronic cassette 40 according to the first exemplary embodiment and the second exemplary embodiment, automatic adjustment of the power supply amount from the power source unit 70 is performed by deriving the irradiation amount of radiation that will be irradiated onto the electronic cassette 40 itself within the specific period of time, and deriving the bias voltage to be applied to the sensor portions 13, or the charge amplifier drive number (namely the radiation detection sensitivity), according to the derived radiation irradiation amount. In contrast thereto, in the electronic cassette according to the third exemplary embodiment, the irradiation amount of radiation that will be irradiated onto the electronic cassette 40 itself within the specific period of time is derived, and the derived irradiation amount is notified to a radiographer in a configuration enabling manual adjustment of radiation detection sensitivity.

Figure 21:
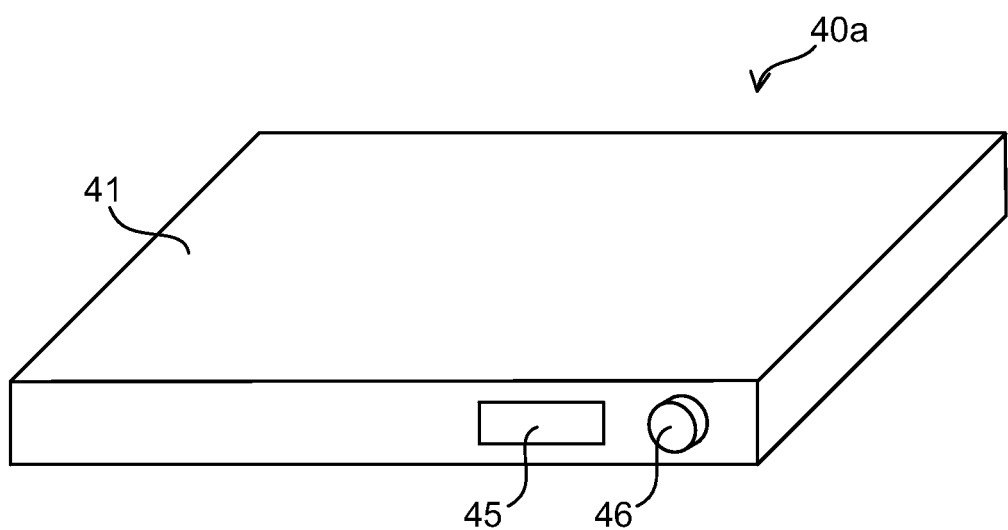
FIG. 21 is a perspective view illustrating a configuration of an electronic cassette according to another exemplary embodiment of the present invention.
Figure 22:
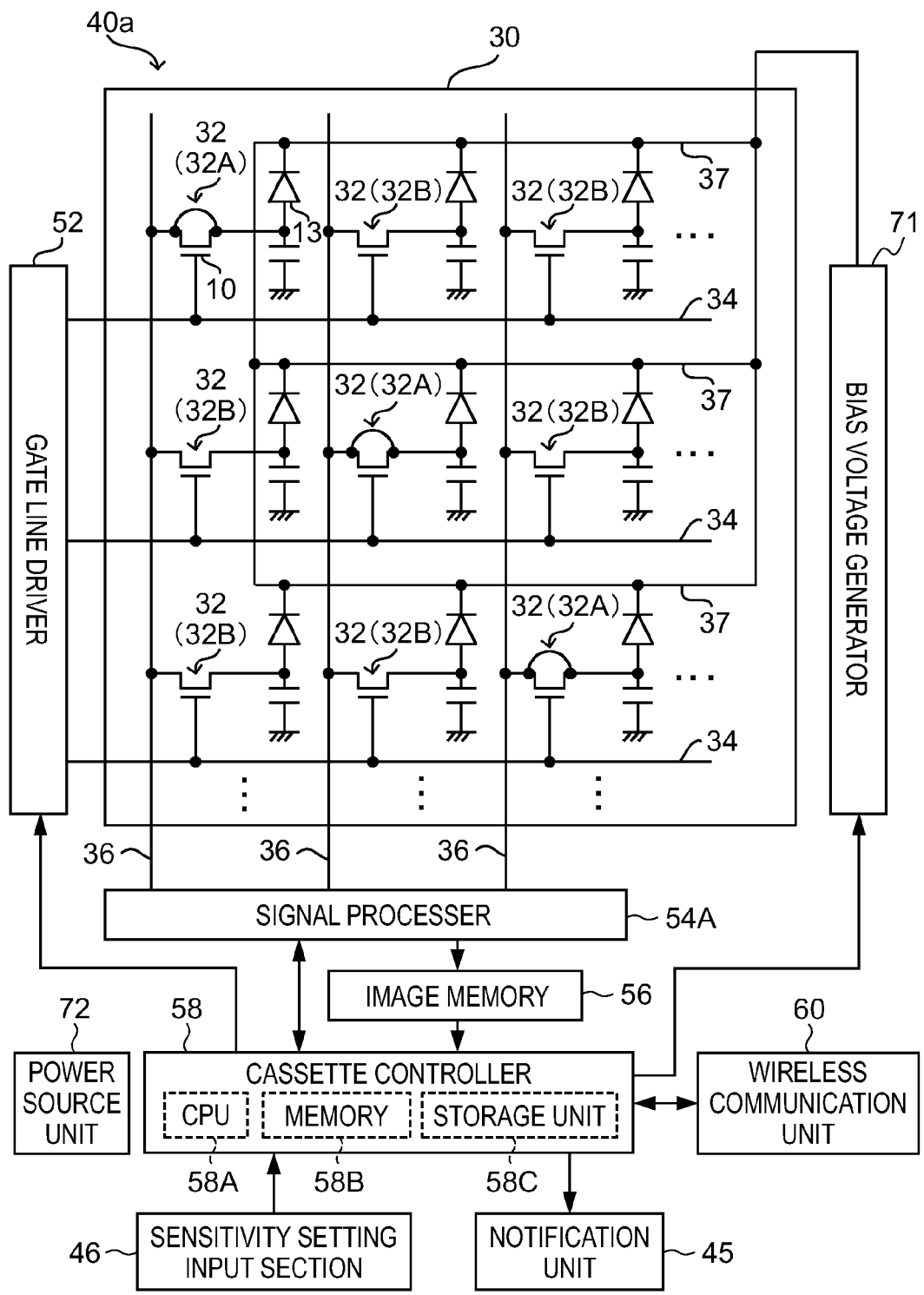
FIG. 22 is a block diagram illustrating relevant configuration of an electrical system of an electronic cassette according to another exemplary embodiment of the present invention.

FIG. 21 is a perspective view of an electronic cassette 40a according to the third exemplary embodiment of the present invention, and FIG. 22 is a diagram illustrating configuration of relevant portions of an electrical system of the electronic cassette 40a. The electronic cassette 40a according to the present exemplary embodiment includes a notification unit 45 and a sensitivity setting input section 46 on the front face of a housing 41.

The notification unit 45 is a unit for notifying the radiographer of the irradiation amount of radiation that will be irradiated onto the electronic cassette 40a within the specific period of time derived by the cassette controller 58 based on the imaging subject data and the exposure conditions. The notification unit 45 is, for example, a display that displays the radiation irradiation amount derived by the cassette controller 58. A radiographer is able to ascertain the irradiation amount of radiation that will be irradiated onto the electronic cassette 40a prior to emission of radiation from the radiation source 121 by a display of the notification unit 45. Note that the notification unit 45 may be configured to include a speaker so as to notify the radiation irradiation amount by voice.

The sensitivity setting input section 46 is for manual adjustment of the magnitude of the bias voltage output from the bias voltage generator 71 and, for example, includes an adjustment knob configuration. For example, configuration may be made such that the bias voltage output from the bias voltage generator 71 is made larger by rotating the adjustment knob configuring the sensitivity setting input section 46 to the right, and the bias voltage is made smaller by rotating to the left. A radiographer is thereby able to determine the bias voltage (radiation detection sensitivity) needed to detect the radiation irradiation start based on the radiation irradiation amount notified by the notification unit 45, and able to set the desired bias voltage (radiation detection sensitivity) by operating the sensitivity setting input section 46. The power supply amount from the power source unit 70 is thereby set accompanying setting of the bias voltage. Note that the sensitivity setting input section 46 may be any configuration capable of adjusting the bias voltage manually, and may include a configuration other than an adjustment knob.

Figure 23:
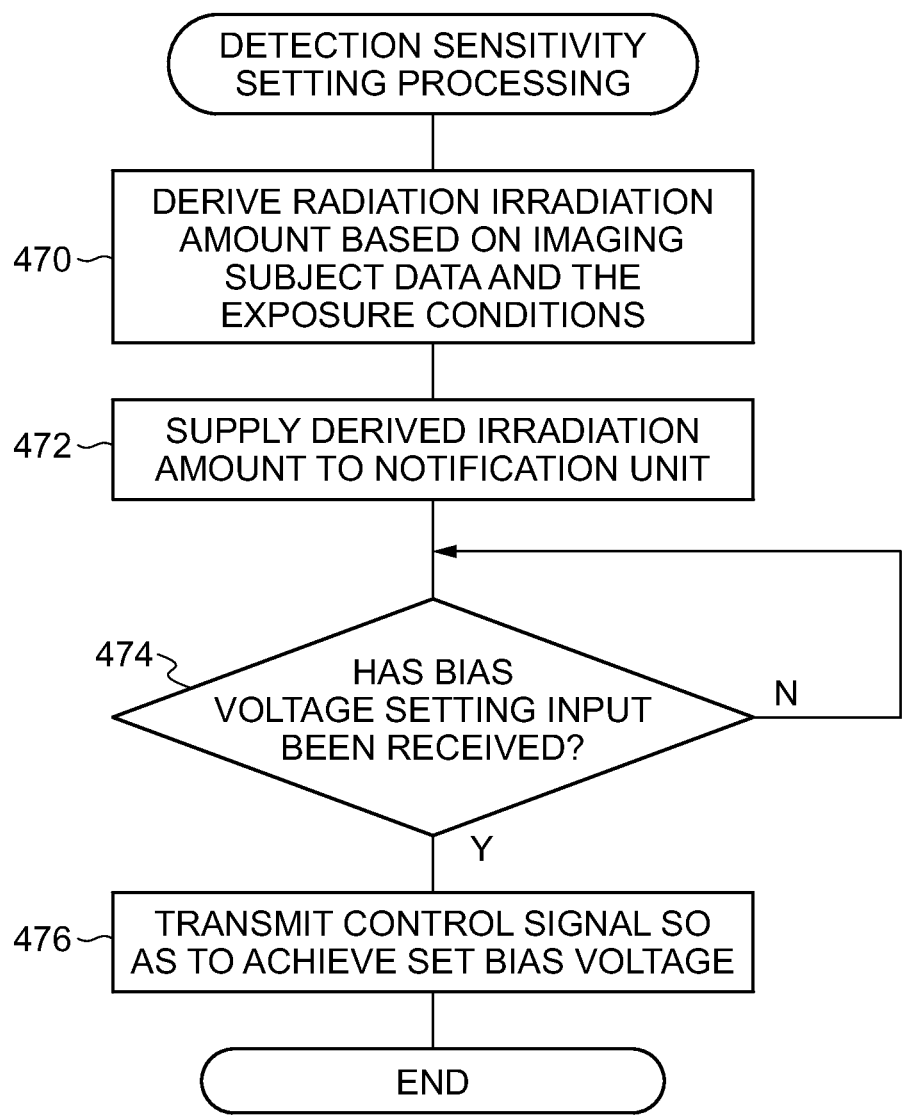
FIG. 23 is a flow chart illustrating a flow of processing in a detection sensitivity setting processing program according to another exemplary embodiment of the present invention.

Explanation follows regarding a detection sensitivity setting processing program according to the present exemplary embodiment executed at step 402 in the cassette imaging processing program illustrated in FIG. 14, with reference to FIG. 23. FIG. 23 is a flow chart illustrating a flow of processing of the detection sensitivity setting processing program according to the present exemplary embodiment executed by the CPU 58A of the cassette controller 58, and corresponds to the flow chart according to the detection sensitivity setting processing program according to the first exemplary embodiment illustrated in FIG. 15.

At step 470, the CPU 58A derives the irradiation amount of radiation that will be irradiated onto the electronic cassette 40a within the specific period of time by searching the first reference table 500 (see FIG. 10) stored in the storage unit 58C using as keys the imaging target site as the imaging subject data, and the tube current and the tube voltage as the exposure conditions, that are contained in initial information supplied from the console 110.

At the next step 472, the CPU 58A supplies the radiation irradiation amount derived at step 470 to the notification unit 45. The notification unit 45 accordingly displays the radiation irradiation amount derived by the CPU 58A at step 470.

At the next step 474 the CPU 58A awaits input of a setting operation of the bias voltage. On display of the radiation irradiation amount on the notification unit 45, the radiographer can decide on the bias voltage needed to detect radiation irradiation start based on the radiation irradiation amount displayed on the notification unit 45, and the decided bias voltage can be set by operation of the sensitivity setting input section 46. The radiographer performs an operation such as depressing a setting complete button provided to the electronic cassette 40a, and then processing transitions to the next step 476.

At the next step 476, the CPU 58A supplies a control signal needed to apply to the sensor portions 13 the bias voltage set through the sensitivity setting input section 46 at step 474, controls the output voltage of the bias voltage generator 71, and then ends the present detection sensitivity setting processing program. The bias voltage generator 71, on receipt of this control signal, outputs the bias voltage set by operation of the sensitivity setting input section 46, and this bias voltage is applied to each of the sensor portions 13.

In this manner, the electronic cassette 40a according to the present exemplary embodiment derives, based on the imaging subject data and the exposure conditions supplied from the console 110, the irradiation amount of radiation that will be irradiated onto the electronic cassette 40a within the specific period of time prior to emission of radiation from the radiation source 121 actually being performed, and displays the derived radiation irradiation amount on the notification unit 45. The radiographer is thereby able to ascertain the irradiation amount of radiation to be irradiated to the electronic cassette 40a prior to emission of radiation from the radiation source 121 actually being performed. The magnitude of the bias voltage applied to the sensor portions 13 can accordingly be adjusted to the desired magnitude by operating the detection sensitivity setting input section 46.

Moreover, according to the electronic cassette 40a of the present exemplary embodiment, the radiographer is able to determine the bias voltage (radiation detection sensitivity) required to detect radiation irradiation start from the radiation irradiation amount displayed on the notification unit 45, enabling the radiographer to set a given bias voltage (radiation detection sensitivity) decided upon by the radiographer by operating the sensitivity setting input section 46. Namely, the electronic cassette 40a of the present exemplary embodiment enables sensitivity setting that utilizes the experience and skills of the radiographer.

Note that configuration may be made such that the CPU 58A derives a radiation irradiation amount based on the imaging subject data and the exposure conditions and derives recommended setting values of bias voltage according to the derived irradiation amount, and displays these derived recommended setting values on the notification unit 45. In order to derive the recommended setting values of bias voltage, for example, the second reference table 501 of the first exemplary embodiment described above may be employed.

The electronic cassette 40a may be configured to be capable of being switched between a manual mode in which the bias voltage is set manually as in the present exemplary embodiment, or an automatic mode performed as in the first exemplary embodiment.

Moreover, in the above exemplary embodiment an example is given of a case in which the detection sensitivity to radiation irradiation start is set in the electronic cassette 40 by setting the bias voltage, however configuration may be made such that the radiation detection sensitivity is changed according to the power supply amount by another parameter, such as for example by setting the drive number or the gain of the charge amplifiers.

Fourth Exemplary Embodiment

Explanation follows regarding a radiographic imaging system according to a fourth exemplary embodiment of the present invention. Explanation has been given in the third exemplary embodiment of an example in which the notification unit 45 and the sensitivity setting input section 46 are provided to the electronic cassette 40a, however in the present exemplary embodiment the functions of a notification unit 45 and a sensitivity setting input section 46 are provided to a console 110.

Figure 24:
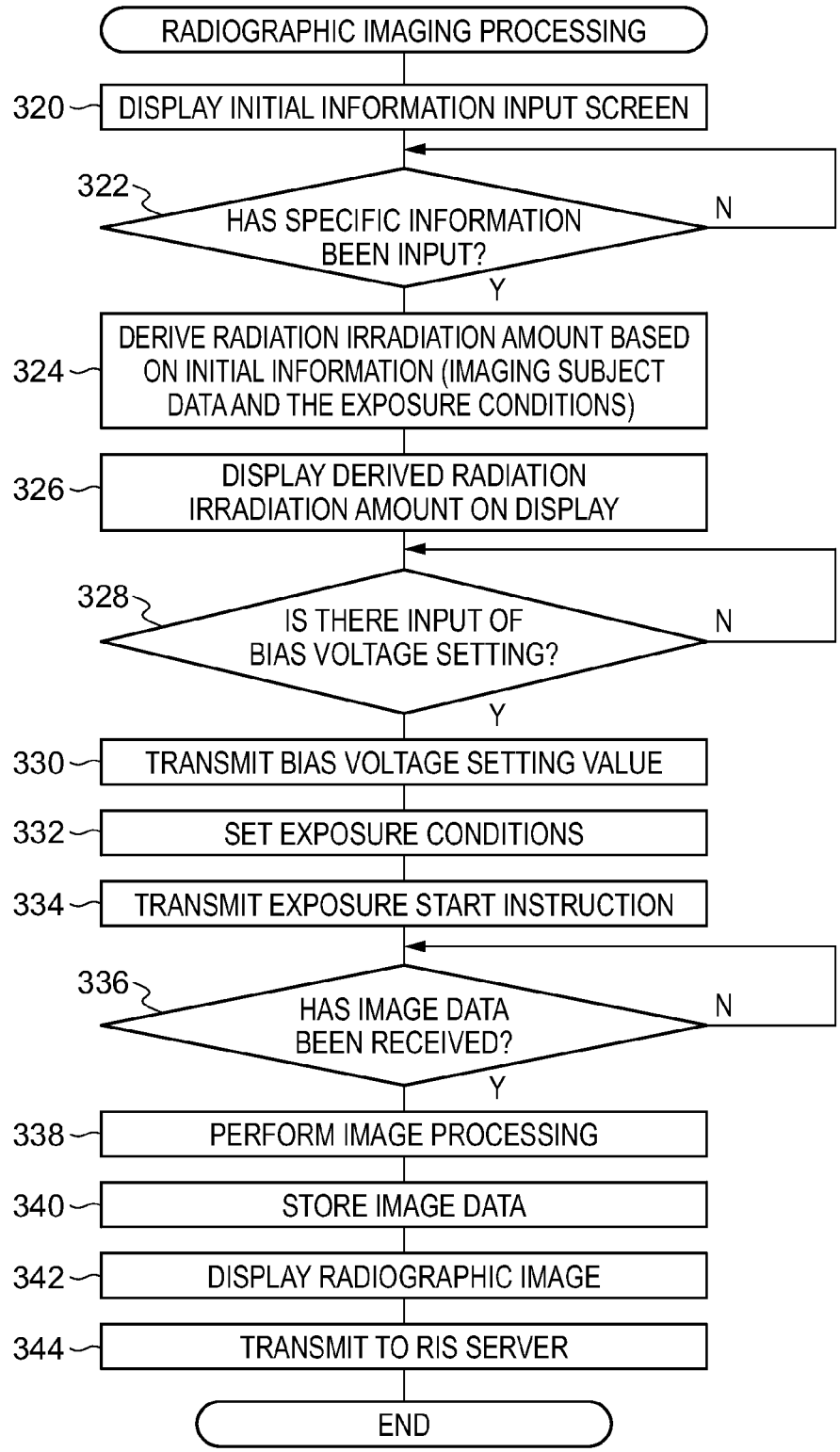
FIG. 24 is a flow chart illustrating a flow of processing in a radiographic imaging processing program according to another exemplary embodiment of the present invention.

FIG. 24 is a flow chart illustrating a flow of processing of a radiographic imaging processing program executed by the CPU 113 of the console 110 according to the present exemplary embodiment. Note that in the present exemplary embodiment a first reference table such as the one illustrated in FIG. 10 is pre-installed in the ROM 114 of the console 110.

At step 320, the CPU 113 controls the display driver 117 such that an initial information input screen such as the example illustrated in FIG. 13 is displayed by a display 111 of the console 110, and then awaits input of specific data at the next step 322.

The radiographer inputs as initial information imaging subject data, including the name of the patient subject to imaging (the imaging subject), the imaging target site, the posture during imaging, and exposure conditions, through an operation panel 112. Then determination is affirmative at step 322 when the radiographer selects an INPUT COMPLETE button displayed in the vicinity of the bottom edge of the initial information input screen, and processing transitions to step 324.

At step 324 the CPU 113 searches a first reference table 500 stored in the ROM 114 using as keys the imaging target site as the imaging subject data, and the tube current and the tube voltage as the exposure conditions, that are contained in initial information that has been input, and derives an irradiation amount of radiation that will be irradiated onto the electronic cassette 40 within the specific period of time.

In the next step 326, the CPU 113 controls the display driver 117 such that the radiation irradiation amount derived at step 324 is displayed on the display 111. The radiation irradiation amount derived at step 324 is thereby displayed on the display 111.

In the next step 328, the CPU 113 awaits input of setting values for the bias voltage. The irradiation amount of radiation that will be irradiated onto the electronic cassette is displayed on the display 111, and the radiographer decides on the bias voltage the electronic cassette 40 needs to detect radiation irradiation start based on the irradiation amount displayed on the display 111, and is able to input the setting value of the decided bias voltage by operating the operation panel 112. Processing transitions to the next step 330 when the radiographer has performed bias voltage setting value input through the operation panel 112.

In the next step 330, the CPU 113 transmits the setting value of the bias voltage input by the radiographer at step 328 to the electronic cassette through the wireless communication unit 119. When the electronic cassette has received the bias voltage setting value from the console 110, the CPU 58A of the electronic cassette 40 supplies the bias voltage generator 71 with a control signal to apply the received setting value for the bias voltage to the sensor portions 13, thereby controlling the output voltage of the bias voltage generator 71.

The processing from step 332 onwards is similar to the processing in step 306 to step 318 of the flow chart of the first exemplary embodiment (FIG. 12) described above and so explanation thereof is omitted.

Thus according to the radiographic imaging system of the present exemplary embodiment, the processing load to the electronic cassette 40 can be reduced due to executing the processing to derive the irradiation amount of radiation that will be irradiated onto the electronic cassette 40 within the specific period of time and the input operation to set the bias voltage on the console 110 side. As a result, the power consumption of the electronic cassette 40 can be reduced. Moreover, the notification unit 45 and the sensitivity setting input section 46 of the third exemplary embodiment do not need to be provided to the electronic cassette even in cases in which manual setting of the detection sensitivity to radiation irradiation start is performed according to the radiographic imaging system of the present exemplary embodiment. Consequently, the configuration for the electronic cassette 40 can be simplified in comparison to that of the third exemplary embodiment.

Figure 25:
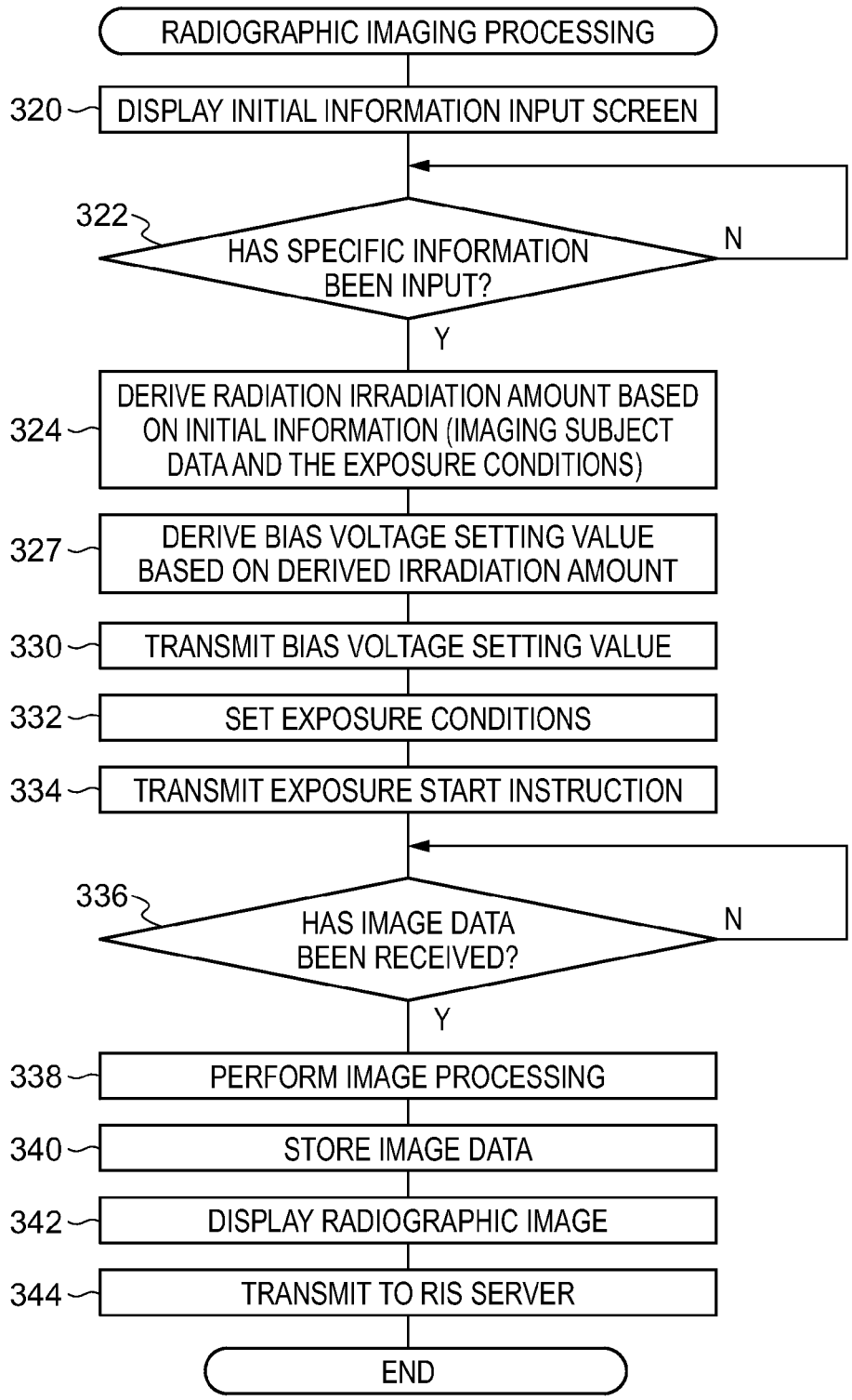
FIG. 25 is a flow chart illustrating a flow of processing in a radiographic imaging processing program according to another exemplary embodiment of the present invention.

Note that in the above the bias voltage is manually set by the radiographer operating the operation panel 112, however configuration may be made such that the CPU 113 of the console 110 derives a setting value of the bias voltage based on the irradiation amount of radiation that will be irradiated onto the electronic cassette 40 derived at step 324, and transmits the derived bias voltage setting value to the electronic cassette 40. FIG. 25 is a flow chart illustrating a flow of processing in the console 110 in such a case. In the flow chart of FIG. 25, the processing of step 326 and step 328 illustrated in FIG. 24 is eliminated, and processing to derive the bias voltage setting value based on the irradiation amount of radiation that will be irradiated onto the electronic cassette 40 derived at step 324 is added at step 327. To derive the bias voltage setting value, the CPU 113 may, for example, employ the second reference table 501 of the first exemplary embodiment. Namely, the CPU 113 derives a bias voltage with a value that is smaller the larger the radiation irradiation amount derived at step 324. Moreover, the setting value of the bias voltage derived by the CPU 113 may be displayed as a recommended setting value on the display 111. Moreover, configuration may be made such that the processing program of the console 110 can switch between an automatic mode in which the bias voltage setting is derived by the CPU 113, and a manual mode in which it is decided by the radiographer.

Moreover, an example has been explained above of a case in which the detection sensitivity to radiation irradiation start of the electronic cassette 40 is set by performing bias voltage setting, however configuration may be made with other parameters that change the radiation detection sensitivity according to the power supply amount, such as for example by setting the drive number or the gain of the charge amplifiers.

Moreover, in each of the exemplary embodiments examples have been given of cases in which the radiation irradiation amount is derived based on both the imaging subject data and the exposure conditions, however the radiation irradiation amount may be derived based on any one of the imaging subject data or the exposure conditions.

Moreover, in each of the exemplary embodiments explanation has been given of cases in which the radiation detection pixels 32A are configured by shorting the sources and drains of the thin film transistors 10, however the present invention is not limited thereto and may, for example, be configured with direct read lines connected to the capacitors 9, and with processing in the signal processor 54 to read charges accumulated in the capacitors 9 from the direct read lines.

In each of the exemplary embodiments described above, explanation has been given of cases in which some of the pixels 32 provided to the radiation detector 20 are employed for the radiation detection pixels 32A, however the present invention is not limited thereto. For example, the radiation detector 20 may have a stacked configuration with the radiation detection pixels 32A in a separate layer to the pixels 32. In such cases, the quality of radiographic images can be raised in comparison to the above exemplary embodiments since there are no missing pixels.

Figure 26A:
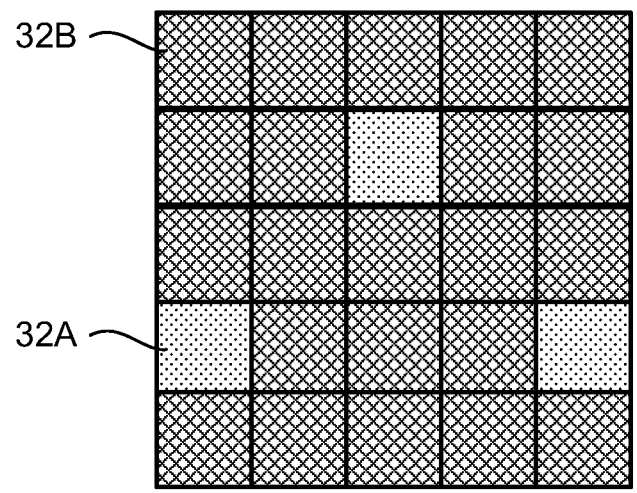
FIG. 26A and FIG. 26B are plan views illustrating disposal of radiation detection pixels according to other exemplary embodiments of the present invention.
Figure 26B:
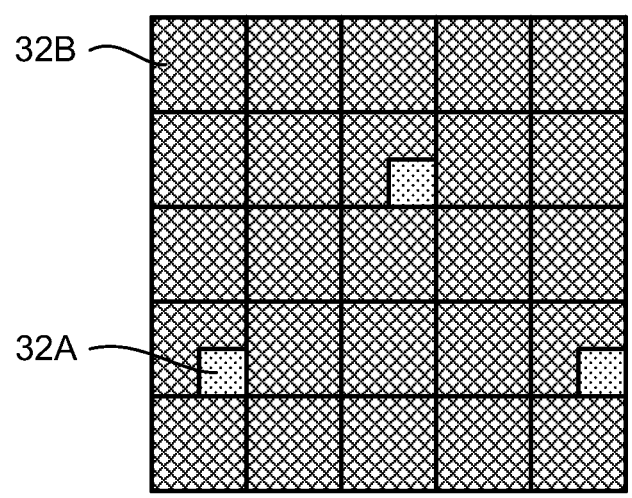

Moreover, in the above exemplary embodiments explanation has been given of cases in which some of the radiographic imaging pixels 32B are applied as the radiation detection pixels 32A, as shown in the example in FIG. 26A, however the present invention is not limited thereto and the radiation detection pixels 32A may be provided in gaps between the radiographic imaging pixels 32B, for example as shown in the example in FIG. 26B. In such cases, the sensitivity of the radiographic imaging pixels 32B provided at positions corresponding to the radiation detection pixels 32A decreases since the surface area of these radiographic imaging pixels 32B decreases, however the quality of radiographic images can be increased since these pixels can also be used for radiographic image detection.

The sensors for detecting radiation do not necessarily have to be applied to the pixels of the radiation detector 20, and configuration may be made such that radiation irradiation start is detected by designated radiation detection sensors that generate charge on irradiation with radiation, provided for example between each row of pixels in the radiation detector 20, or at predetermined positions in peripheral positions. In such cases, such sensors do not necessarily have to be provided to the radiation detector 20, and may be disposed as a separate body to the radiation detector 20.

In the above exemplary embodiments, explanation has been given of cases in which the radiation detection pixels 32A and the radiographic imaging pixels 32B are provided separately to one another, however the present invention is not limited thereto. Configuration may be made wherein the radiographic imaging pixels 32B are applied as sensors that determine whether or not radiation has been detected, without providing the radiation detection pixels 32A. Namely, configuration may be made with the sensors that determine whether or not radiation has been detected being common to the radiographic imaging pixels 32B. In such cases, the present invention can be achieved simply, without the need to provide extra sensors.

In the above exemplary embodiments, explanation has been given of cases in which the sensor portions 13 are configured including an organic photoelectric conversion material that generates charge upon receiving light generated by the scintillator 8. The present invention is not limited thereto, and configuration may be made wherein the sensor portions 13 do not include an organic photoelectric conversion material. For example, the sensor portions 13 may employ a semiconductor such as amorphous selenium, in a configuration wherein radiation is converted directly into charge.

In the above exemplary embodiments, explanation has been given of cases in which the case 42 that houses the cassette controller 58 and the power source unit 70 is disposed inside the housing 41 of the electronic cassette 40 so as not to overlap with the radiation detector 20, however there is no limitation thereto. The radiation detector 20 may for example be disposed so as to overlap with the cassette controller 58 and/or the power source unit 70.

In the above exemplary embodiments, explanation has been given of cases in which wireless communication is performed between the electronic cassette 40 and the console 110, and between the radiation generator 120 and the console 110, however the present invention is not limited thereto, and wired communication may be performed between the electronic cassette 40 and the console 110 and/or between the radiation generator 120 and the console 110.

In the above exemplary embodiments, explanation has been given of cases in which X-rays are applied as the radiation, however the present invention is not limited thereto and other radiation such as gamma rays may be applied as the radiation.

Other configurations of the RIS 100 (see FIG. 1), the radiographic imaging room 180 (see FIG. 2), the electronic cassette 40 (see FIG. 3 to FIG. 8) and the imaging systems 104 (see FIG. 9) described in the above exemplary embodiments are merely examples thereof. Obviously, for example, unnecessary portions may be omitted, new portions added, and connection states changed within a scope not departing from the spirit of the present invention.

Moreover, the flow of processing in each of the programs described in the above exemplary embodiments (see FIG. 12, FIG. 14, FIG. 15, FIG. 20) are also merely examples thereof, and obviously unnecessary steps may be omitted, new steps added, and processing sequences varied within a scope not departing from the spirit of the present invention.

Each of the controls for adjusting the detection sensitivity in the detection of radiation irradiation start illustrated in each of the above exemplary embodiments may be combined as appropriate. For example, it is possible to execute a combination of control to adjust the bias voltage applied to the sensor portions 13 illustrated in the first exemplary embodiment and control to adjust the drive number of the charge amplifiers 92 illustrated in the second exemplary embodiment.

What is claimed is:

1. A radiographic imaging device comprising:
   a detector that detects an irradiation start of radiation irradiated during imaging of a radiographic image;
   a derivation unit that derives an irradiation amount of radiation that will be irradiated within a specific period of time based on input data;
   a controller that causes a power supply amount to the detector to become smaller and detection sensitivity to irradiation start in the detector, to become lower as the radiation irradiation amount derived by the derivation unit increases, wherein the controller is different from the detector; and
   an imaging unit that images the radiographic image after radiation irradiation start has been detected by the detector, wherein:
   the detector includes a plurality of sensor portions that each generate charge according to an irradiation amount of the radiation, and a signal processing section that generates an electrical signal according to amounts of charge generated in the plurality of sensor portions;
   the controller causes a number of the sensor portions that are active, out of the plurality of sensor portions, to decrease and causes the power supply amount to the detector to decrease, as the radiation irradiation amount derived by the derivation unit increase; and wherein:
   the signal processing section includes a plurality of operation amplification circuits respectively provided to correspond to each of the plurality of sensor portions; and
   the controller causes a drive number of the operation amplification circuits to decrease, as the radiation irradiation amount derived by the derivation unit increases.

2. The radiographic imaging device of claim 1, wherein:
   the controller controls the detection sensitivity to radiation in the imaging unit during imaging of a radiographic image independent of the detection sensitivity to radiation at the irradiation start in the detector.

3. The radiographic imaging device of claim 1, wherein:
   the detector includes a sensor portion that generates charge in an amount that is based on an irradiation amount of the radiation and that changes sensitivity according to bias voltage applied, and a bias voltage generator that generates a bias voltage to apply to the sensor portion; and
   the controller causes the bias voltage to decrease and causes the power supply amount to the detector to decrease, as the radiation irradiation amount derived by the derivation unit becomes larger.

4. The radiographic imaging device of claim 1, wherein:
   the detector includes a plurality of sensor portions that each generate charge according to an irradiation amount of the radiation, and a signal processing section that generates an electrical signal according to amounts of charge generated in the plurality of sensor portions; and
   the controller causes a power supply amount to the signal processing section to decrease, as the radiation irradiation amount derived by the derivation unit increases.

5. The radiographic imaging device of claim 4, wherein:
the signal processing section includes a plurality of operation amplification circuits respectively provided to correspond to each of the plurality of sensor portions; and
the controller causes a drive number of the operation amplification circuits to decrease as the radiation irradiation amount derived by the derivation unit increases.

6. The radiographic imaging device of claim 1, wherein
the controller includes a storage unit stored with a plurality of detection sensitivity settings for the detector, and selects one of the plurality of detection sensitivity settings stored in the storage unit according to the radiation irradiation amount derived by the derivation unit.

7. The radiographic imaging device of claim 1, wherein
the derivation unit derives an irradiation amount to be irradiated onto an irradiation face within the specific period of time of radiation emitted from a radiation source and attenuated on passing through an imaging subject that is an imaging target of the radiographic image.

8. The radiographic imaging device of claim 1, wherein
the derivation unit derives an irradiation amount of the radiation using as input data at least one of imaging subject data relating to the imaging subject that is an imaging target of the radiographic image or an exposure condition of a radiation source.

9. The radiographic imaging device of claim 8, wherein
the imaging subject data includes an imaging target site of the imaging subject; and
the exposure condition includes at least one of a tube voltage or a tube current.

10. The radiographic imaging device of claim 8, further comprising:
a reception unit that receives at least one input of the imaging subject data or the exposure condition.

11. The radiographic imaging device of claim 2, wherein:
the detector includes a sensor portion that is employed for irradiation start detection; and
the radiographic image imaging unit includes a sensor portion that is employed for imaging a radiographic image and is separate to the sensor portion that is employed for the irradiation start detection.

12. A radiographic imaging system comprising:
a radiographic imaging device including a detector that detects an irradiation start of radiation irradiated during imaging a radiographic image and that changes in detection sensitivity to the radiation according to a magnitude of power supplied, a reception unit that receives a setting input of detection sensitivity to radiation of the detector, a controller that sets the detection sensitivity received by the reception unit as the detection sensitivity to radiation of the detector, and an imaging unit that images the radiographic image after irradiation start has been detected by the detector; and
a control device including a first derivation unit that derives an irradiation amount of radiation that will be irradiated onto the radiographic imaging device within a specific period of time based on input data, a second derivation unit that derives a setting for detection sensitivity to radiation at the irradiation start in the detector such that a power supply amount to the detector is smaller the larger the radiation irradiation amount derived by the first derivation unit, and a supply unit that supplies the reception unit with the detection sensitivity setting derived by the second derivation unit, wherein the control device is different from the detector.

13. A radiation irradiation start detection sensitivity control method comprising:
deriving an irradiation amount of radiation that will be irradiated within a specific period of time in imaging a radiographic image based on input data; and
making, by utilizing a controller, a power supply amount smaller to a detector that detects irradiation start of the radiation and lowering detection sensitivity to radiation irradiation start in the detector the larger the derived radiation irradiation amount, wherein the controller is different from the detector, wherein:
the detector includes a plurality of sensor portions that each generate charge according to an irradiation amount of the radiation, and a signal processing section that generates an electrical signal according to amounts of charge generated in the plurality of sensor portions;
the controller causes a number of the sensor portions that are active, out of the plurality of sensor portions, to decrease and causes the power supply amount to the detector to decrease, as the radiation irradiation amount derived by the derivation unit increase; and wherein:
the signal processing section includes a plurality of operation amplification circuits respectively provided to correspond to each of the plurality of sensor portions; and
the controller causes a drive number of the operation amplification circuits to decrease, as the radiation irradiation amount derived by the derivation unit increases.

* * * * *